US009585593B2

(12) United States Patent
Fan et al.

(10) Patent No.: US 9,585,593 B2
(45) Date of Patent: Mar. 7, 2017

(54) SIGNAL DISTRIBUTION FOR PATIENT-ELECTRODE MEASUREMENTS

(76) Inventors: Chung Shing Fan, Toronto (CA); Joel Ironstone, Toronto (CA); Kenneth Carless Smith, Toronto (CA)

( * ) Notice: Subject to any disclaimer, the term of this patent is extended or adjusted under 35 U.S.C. 154(b) by 1175 days.

(21) Appl. No.: 13/508,655

(22) PCT Filed: Nov. 18, 2010

(86) PCT No.: PCT/AU2010/001552
§ 371 (c)(1),
(2), (4) Date: Jan. 4, 2013

(87) PCT Pub. No.: WO2011/060497
PCT Pub. Date: May 26, 2011

(65) Prior Publication Data
US 2013/0102920 A1  Apr. 25, 2013

(30) Foreign Application Priority Data

Nov. 18, 2009 (AU) ................................ 2009905642

(51) Int. Cl.
*A61B 5/05* (2006.01)
*A61B 5/053* (2006.01)
(Continued)

(52) U.S. Cl.
CPC ............ *A61B 5/053* (2013.01); *A61B 5/0537* (2013.01); *A61B 5/4869* (2013.01);
(Continued)

(58) Field of Classification Search
CPC ..... A61B 5/053; A61B 5/0537; A61B 5/4869; A61B 5/4875; A61B 5/4878;
(Continued)

(56) References Cited

U.S. PATENT DOCUMENTS 3,316,896 A   5/1967  Thomasset
3,851,641 A  12/1974  Toole
(Continued)

FOREIGN PATENT DOCUMENTS

CA   2231038   11/1999
CA   2638958    6/2000
(Continued)

OTHER PUBLICATIONS

Abdullah M. Z.; Simulation of an inverse problem in electrical impedance tomography using resistance electrical network analogues; International Journal of Electrical Engineering Education; vol. 36, No. 4, pp. 311-324; Oct. 1999.
(Continued)

*Primary Examiner* — Devin Henson
(74) *Attorney, Agent, or Firm* — Knobbe Martens Olson & Bear LLP

(57) ABSTRACT

Apparatus for electrically connecting measurement apparatus to a biological subject, the apparatus including a signal delivery circuit including a current buffer having a current buffer input for receiving a signal from a signal source and a current buffer output for supplying a current to an electrode attached to the biological subject, and a voltage buffer having a voltage buffer input coupled to the current buffer output and a voltage buffer output for providing a voltage signal indicative of a voltage at the electrode, to a sensor.

24 Claims, 9 Drawing Sheets

(51) Int. Cl.
| | |
|---|---|
| G01R 31/00 | (2006.01) |
| G01R 27/02 | (2006.01) |
| A61B 5/00 | (2006.01) |
| H03F 3/50 | (2006.01) |
| H03F 3/60 | (2006.01) |
| G01R 1/30 | (2006.01) |

(52) U.S. Cl.
CPC .......... *A61B 5/4875* (2013.01); *A61B 5/4878* (2013.01); *A61B 5/6843* (2013.01); *A61B 5/6885* (2013.01); *A61B 5/7203* (2013.01); *G01R 1/30* (2013.01); *G01R 27/02* (2013.01); *G01R 31/00* (2013.01); *H03F 3/50* (2013.01); *H03F 3/602* (2013.01); *H03F 2200/261* (2013.01)

(58) Field of Classification Search
CPC ... A61B 5/7203; A61B 5/6843; A61B 5/6885; G01R 1/30; G01R 27/02; G01R 31/00; H03F 3/50; H03F 3/602; H03F 2200/261
See application file for complete search history.

(56) References Cited

U.S. PATENT DOCUMENTS

| | | |
|---|---|---|
| 3,866,600 A | 2/1975 | Rey |
| 3,868,165 A | 2/1975 | Gonser |
| 3,871,359 A | 3/1975 | Pacela |
| 4,008,712 A | 2/1977 | Nyboer |
| 4,034,854 A | 7/1977 | Bevilacqua |
| 4,082,087 A | 4/1978 | Howson |
| 4,121,575 A | 10/1978 | Mills et al. |
| 4,144,878 A | 3/1979 | Wheeler |
| RE30,101 E | 9/1979 | Kubicek et al. |
| 4,169,463 A | 10/1979 | Piquard |
| 4,184,486 A | 1/1980 | Papa |
| 4,233,987 A | 11/1980 | Feingold |
| 4,291,708 A | 9/1981 | Frei et al. |
| 4,314,563 A | 2/1982 | Wheeler |
| 4,353,372 A | 10/1982 | Ayer |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,638,807 A | 1/1987 | Ryder |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,832,608 A | 5/1989 | Kroll |
| 4,836,214 A | 6/1989 | Sramek |
| 4,890,630 A | 1/1990 | Kroll et al. |
| 4,895,163 A | 1/1990 | Libke et al. |
| 4,899,758 A | 2/1990 | Finkelstein et al. |
| 4,905,705 A | 3/1990 | Kizakevich et al. |
| 4,911,175 A | 3/1990 | Shizgal |
| 4,922,911 A | 5/1990 | Wada et al. |
| 4,924,875 A | 5/1990 | Chamoun |
| 4,942,880 A | 7/1990 | Slovák |
| 4,951,682 A | 8/1990 | Petre |
| 4,981,141 A | 1/1991 | Segalowitz |
| 5,020,541 A | 6/1991 | Marriott |
| 5,025,784 A | 6/1991 | Shao et al. |
| 5,063,937 A | 11/1991 | Ezenwa et al. |
| 5,078,134 A | 1/1992 | Heilman et al. |
| 5,086,781 A | 2/1992 | Bookspan |
| 5,101,828 A | 4/1992 | Welkowitz et al. |
| 5,143,079 A | 9/1992 | Frei et al. |
| 5,184,624 A | 2/1993 | Brown et al. |
| 5,197,479 A | 3/1993 | Hubelbank et al. |
| 5,199,432 A | 4/1993 | Quedens et al. |
| 5,233,982 A | 8/1993 | Kohl |
| 5,246,008 A | 9/1993 | Mueller |
| 5,272,624 A | 12/1993 | Gisser et al. |
| 5,280,429 A | 1/1994 | Withers |
| 5,282,840 A | 2/1994 | Hudrlik |
| 5,284,142 A | 2/1994 | Goble et al. |
| 5,305,192 A | 4/1994 | Bonte et al. |
| 5,309,917 A | 5/1994 | Wang et al. |
| 5,311,878 A | 5/1994 | Brown et al. |
| 5,335,667 A | 8/1994 | Cha et al. |
| 5,351,697 A | 10/1994 | Cheney et al. |
| 5,353,802 A | 10/1994 | Ollmar |
| 5,372,141 A | 12/1994 | Gallup et al. |
| 5,381,333 A | 1/1995 | Isaacson et al. |
| 5,390,110 A | 2/1995 | Cheney et al. |
| 5,415,164 A | 5/1995 | Faupel |
| 5,421,345 A | 6/1995 | Lekholm et al. |
| 5,423,326 A | 6/1995 | Wang et al. |
| 5,427,113 A | 6/1995 | Hiroshi et al. |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,511,553 A | 4/1996 | Segalowitz |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,562,607 A | 10/1996 | Gyory |
| 5,575,929 A | 11/1996 | Yu et al. |
| 5,588,429 A | 12/1996 | Isaacson et al. |
| 5,611,351 A | 3/1997 | Sato et al. |
| 5,615,689 A | 4/1997 | Kotler |
| 5,626,146 A | 5/1997 | Barber et al. |
| 5,704,355 A | 1/1998 | Bridges |
| 5,730,136 A | 3/1998 | Laufer et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,876,353 A | 3/1999 | Riff |
| 5,919,142 A | 7/1999 | Boone et al. |
| 5,947,910 A | 9/1999 | Zimmet |
| 5,957,861 A | 9/1999 | Combs et al. |
| 5,964,703 A | 10/1999 | Goodman et al. |
| 5,994,956 A | 11/1999 | Concorso |
| 6,006,125 A | 12/1999 | Kelly et al. |
| 6,011,992 A | 1/2000 | Hubbard et al. |
| 6,015,389 A | 1/2000 | Brown |
| 6,018,677 A | 1/2000 | Vidrine et al. |
| 6,078,833 A | 6/2000 | Hueber |
| 6,101,413 A | 8/2000 | Olson et al. |
| 6,115,626 A | 9/2000 | Whayne et al. |
| 6,122,544 A | 9/2000 | Organ |
| 6,125,297 A | 9/2000 | Siconolfi |
| 6,129,666 A | 10/2000 | DeLuca et al. |
| 6,142,949 A | 11/2000 | Ubby |
| 6,151,523 A | 11/2000 | Ferrer et al. |
| 6,167,300 A | 12/2000 | Cherepenin et al. |
| 6,173,003 B1 | 1/2001 | Whikehart et al. |
| 6,228,022 B1 | 5/2001 | Friesem et al. |
| 6,228,033 B1 | 5/2001 | Koobi |
| 6,233,473 B1 | 5/2001 | Shepherd et al. |
| 6,236,886 B1 | 5/2001 | Cherepenin et al. |
| 6,248,083 B1 | 6/2001 | Smith et al. |

(56) References Cited

U.S. PATENT DOCUMENTS

| | | |
|---|---|---|
| 6,253,100 B1 | 6/2001 | Zhdanov |
| 6,256,532 B1 | 7/2001 | Cha |
| 6,280,396 B1 | 8/2001 | Clark |
| 6,292,690 B1 | 9/2001 | Petrucelli et al. |
| 6,308,097 B1 | 10/2001 | Pearlman |
| 6,339,722 B1 | 1/2002 | Heethaar et al. |
| 6,354,996 B1 | 3/2002 | Drinan et al. |
| 6,376,023 B1 | 4/2002 | Mori |
| 6,432,045 B2 | 8/2002 | Lemperle et al. |
| 6,459,930 B1 | 10/2002 | Takehara et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,501,984 B1 | 12/2002 | Church et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,532,384 B1 | 3/2003 | Fukuda |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,564,079 B1 | 5/2003 | Cory et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtk |
| 6,633,777 B2 | 10/2003 | Szopinski |
| 6,636,754 B1 | 10/2003 | Baura et al. |
| 6,643,543 B2 | 11/2003 | Takehara et al. |
| 6,658,296 B1 | 12/2003 | Wong et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,760,617 B2 | 7/2004 | Ward et al. |
| 6,763,263 B2 | 7/2004 | Gregory et al. |
| 6,768,921 B2 | 7/2004 | Organ et al. |
| 6,788,966 B2 | 9/2004 | Kenan et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,845,264 B1 | 1/2005 | Skladnev et al. |
| 6,870,109 B1 | 3/2005 | Villarreal |
| 6,875,176 B2 | 4/2005 | Mourad et al. |
| 6,906,533 B1 | 6/2005 | Yoshida |
| 6,922,586 B2 | 7/2005 | Davies |
| 6,936,012 B2 | 8/2005 | Wells |
| 6,940,286 B2 | 9/2005 | Wang et al. |
| RE38,879 E | 11/2005 | Goodman et al. |
| 6,980,852 B2 | 12/2005 | Jersey-Willuhn et al. |
| 6,980,853 B2 | 12/2005 | Miyoshi et al. |
| 7,065,399 B2 | 6/2006 | Nakada |
| 7,079,889 B2 | 7/2006 | Nakada |
| 7,096,061 B2 | 8/2006 | Arad |
| 7,122,012 B2 | 10/2006 | Bouton et al. |
| 7,130,680 B2 | 10/2006 | Kodama et al. |
| 7,132,611 B2 | 11/2006 | Gregaard et al. |
| 7,148,701 B2 | 12/2006 | Park et al. |
| 7,149,573 B2 | 12/2006 | Wang |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,206,630 B1 | 4/2007 | Tarler |
| 7,212,852 B2 | 5/2007 | Smith et al. |
| 7,233,823 B2 | 6/2007 | Simond et al. |
| 7,251,524 B1 | 7/2007 | Hepp et al. |
| 7,288,943 B2 | 10/2007 | Matthiessen et al. |
| D557,809 S | 12/2007 | Neverov et al. |
| 7,313,435 B2 | 12/2007 | Nakada et al. |
| 7,317,161 B2 * | 1/2008 | Fukuda ............... H01B 11/206 174/36 |
| 7,336,992 B2 | 2/2008 | Shiokawa |
| 7,440,796 B2 | 10/2008 | Woo et al. |
| 7,457,660 B2 | 11/2008 | Smith et al. |
| 7,477,937 B2 | 1/2009 | Iijima et al. |
| 7,496,450 B2 | 2/2009 | Ortiz Aleman et al. |
| 7,499,745 B2 | 3/2009 | Littrup et al. |
| D603,051 S | 10/2009 | Causevic et al. |
| 7,603,158 B2 | 10/2009 | Nachman |
| 7,603,171 B2 | 10/2009 | Eror et al. |
| 7,628,761 B2 | 12/2009 | Gozani et al. |
| 7,638,341 B2 | 12/2009 | Rubinsky et al. |
| 7,657,292 B2 | 2/2010 | Baker et al. |
| 7,660,617 B2 | 2/2010 | Davis |
| 7,706,872 B2 | 4/2010 | Min et al. |
| 7,711,418 B2 | 5/2010 | Garber et al. |
| 7,729,756 B2 | 6/2010 | Mertelmeier et al. |
| 7,733,224 B2 | 6/2010 | Tran |
| 7,749,013 B2 | 7/2010 | Sato et al. |
| 7,860,557 B2 | 12/2010 | Istvan et al. |
| 7,917,202 B2 | 3/2011 | Chamney et al. |
| D641,886 S | 7/2011 | Causevic et al. |
| 7,983,853 B2 | 7/2011 | Wang et al. |
| D647,208 S | 10/2011 | Rothman et al. |
| 8,055,335 B2 | 11/2011 | Stylos |
| 8,068,906 B2 | 11/2011 | Chetham |
| 8,172,762 B2 | 5/2012 | Robertson |
| 8,233,617 B2 | 7/2012 | Johnson et al. |
| 8,233,974 B2 | 7/2012 | Ward et al. |
| D669,186 S | 10/2012 | Gozani |
| D669,187 S | 10/2012 | Gozani |
| 8,285,356 B2 | 10/2012 | Bly et al. |
| D674,096 S | 1/2013 | Gaw et al. |
| 8,467,865 B2 | 6/2013 | Gregory et al. |
| 8,744,564 B2 | 6/2014 | Ward et al. |
| D718,458 S | 11/2014 | Vosch et al. |
| D719,660 S | 12/2014 | Vosch et al. |
| D728,801 S | 5/2015 | Machon et al. |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0021799 A1 | 9/2001 | Ohlsson et al. |
| 2001/0025139 A1 | 9/2001 | Pearlman |
| 2001/0051774 A1 | 12/2001 | Littrup et al. |
| 2002/0020138 A1 | 2/2002 | Walker et al. |
| 2002/0022773 A1 | 2/2002 | Drinan et al. |
| 2002/0022787 A1 | 2/2002 | Takehara et al. |
| 2002/0035334 A1 | 3/2002 | Meij et al. |
| 2002/0072686 A1 | 6/2002 | Hoey et al. |
| 2002/0079910 A1 | 6/2002 | Fukuda |
| 2002/0093991 A1 | 7/2002 | Kurihara |
| 2002/0093992 A1 | 7/2002 | Plangger |
| 2002/0106681 A1 | 8/2002 | Wexler et al. |
| 2002/0109621 A1 | 8/2002 | Khair et al. |
| 2002/0111559 A1 | 8/2002 | Kurata et al. |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0193689 A1 | 12/2002 | Bernstein et al. |
| 2002/0194419 A1 | 12/2002 | Rajput et al. |
| 2003/0004403 A1 | 1/2003 | Drinan et al. |
| 2003/0009111 A1 | 1/2003 | Cory et al. |
| 2003/0023184 A1 | 1/2003 | Pitts-Crick et al. |
| 2003/0028221 A1 | 2/2003 | Zhu et al. |
| 2003/0036713 A1 | 2/2003 | Bouton et al. |
| 2003/0050570 A1 | 3/2003 | Kodama et al. |
| 2003/0073916 A1 | 4/2003 | Yonce |
| 2003/0105410 A1 | 6/2003 | Pearlman |
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0176808 A1 | 9/2003 | Masuo |

(56) References Cited

U.S. PATENT DOCUMENTS

| | | |
|---|---|---|
| 2003/0216661 A1 | 11/2003 | Davies |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0059220 A1 | 3/2004 | Mourad et al. |
| 2004/0059242 A1 | 3/2004 | Masuo et al. |
| 2004/0073127 A1 | 4/2004 | Istvan et al. |
| 2004/0073130 A1 | 4/2004 | Bohm et al. |
| 2004/0077944 A1 | 4/2004 | Steinberg et al. |
| 2004/0116819 A1 | 6/2004 | Alt |
| 2004/0127793 A1 | 7/2004 | Mendlein et al. |
| 2004/0158167 A1* | 8/2004 | Smith .................... A61B 5/053 600/547 |
| 2004/0167423 A1 | 8/2004 | Pillon et al. |
| 2004/0171961 A1 | 9/2004 | Smith et al. |
| 2004/0181163 A1 | 9/2004 | Wong et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0220632 A1 | 11/2004 | Burnes |
| 2004/0234113 A1 | 11/2004 | Miga |
| 2004/0236202 A1 | 11/2004 | Burton |
| 2004/0242987 A1 | 12/2004 | Liew et al. |
| 2004/0242989 A1 | 12/2004 | Zhu et al. |
| 2004/0243018 A1 | 12/2004 | Organ et al. |
| 2004/0252870 A1 | 12/2004 | Reeves et al. |
| 2004/0253652 A1 | 12/2004 | Davies |
| 2004/0260167 A1 | 12/2004 | Leonhardt |
| 2004/0267333 A1 | 12/2004 | Kronberg |
| 2004/0267344 A1 | 12/2004 | Stett et al. |
| 2005/0033281 A1 | 2/2005 | Bowman et al. |
| 2005/0039763 A1 | 2/2005 | Kraemer et al. |
| 2005/0049474 A1 | 3/2005 | Kellogg et al. |
| 2005/0080460 A1 | 4/2005 | Wang et al. |
| 2005/0085743 A1 | 4/2005 | Hacker et al. |
| 2005/0098343 A1 | 5/2005 | Fukuda |
| 2005/0101875 A1 | 5/2005 | Semler et al. |
| 2005/0107719 A1 | 5/2005 | Arad et al. |
| 2005/0113704 A1 | 5/2005 | Lawson et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177061 A1 | 8/2005 | Alanen et al. |
| 2005/0177062 A1 | 8/2005 | Skrabal et al. |
| 2005/0192488 A1 | 9/2005 | Bryenton et al. |
| 2005/0201598 A1 | 9/2005 | Harel et al. |
| 2005/0203435 A1 | 9/2005 | Nakada |
| 2005/0203436 A1 | 9/2005 | Davies |
| 2005/0215918 A1 | 9/2005 | Frantz et al. |
| 2005/0228309 A1 | 10/2005 | Fisher et al. |
| 2005/0251062 A1 | 11/2005 | Choi et al. |
| 2005/0261743 A1 | 11/2005 | Kroll |
| 2005/0283091 A1 | 12/2005 | Kink et al. |
| 2006/0004300 A1 | 1/2006 | Kennedy |
| 2006/0025701 A1 | 2/2006 | Kasahara |
| 2006/0041280 A1 | 2/2006 | Stahmann et al. |
| 2006/0047189 A1 | 3/2006 | Takehara |
| 2006/0052678 A1 | 3/2006 | Drinan |
| 2006/0064029 A1 | 3/2006 | Arad (Abboud) |
| 2006/0070623 A1 | 4/2006 | Wilkinson et al. |
| 2006/0085048 A1 | 4/2006 | Cory et al. |
| 2006/0085049 A1 | 4/2006 | Cory et al. |
| 2006/0100532 A1 | 5/2006 | Bae et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0135886 A1 | 6/2006 | Lippert et al. |
| 2006/0184060 A1 | 8/2006 | Belalcazar |
| 2006/0197509 A1 | 9/2006 | Kanamori et al. |
| 2006/0200033 A1 | 9/2006 | Keren et al. |
| 2006/0224079 A1 | 10/2006 | Washchuk |
| 2006/0224080 A1 | 10/2006 | Oku et al. |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0252670 A1 | 11/2006 | Fiorucci et al. |
| 2006/0253016 A1 | 11/2006 | Baker et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | Mcadams |
| 2007/0007975 A1 | 1/2007 | Hawkins et al. |
| 2007/0010758 A1 | 1/2007 | Matthiessen et al. |
| 2007/0024310 A1* | 2/2007 | Tokuno .................. G01R 27/02 324/610 |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0088227 A1 | 4/2007 | Nishimura |
| 2007/0106342 A1 | 5/2007 | Schumann |
| 2007/0118027 A1 | 5/2007 | Baker et al. |
| 2007/0156061 A1 | 7/2007 | Hess |
| 2007/0188219 A1 | 8/2007 | Segarra |
| 2007/0246046 A1 | 10/2007 | Teschner et al. |
| 2007/0270707 A1 | 11/2007 | Belalcazar |
| 2008/0001608 A1 | 1/2008 | Saulnier |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0027350 A1 | 1/2008 | Webler |
| 2008/0039700 A1 | 2/2008 | Drinan et al. |
| 2008/0048786 A1 | 2/2008 | Feldkamp et al. |
| 2008/0051643 A1 | 2/2008 | Park et al. |
| 2008/0064981 A1 | 3/2008 | Gregory |
| 2008/0091114 A1 | 4/2008 | Min et al. |
| 2008/0139957 A1 | 6/2008 | Hubbard et al. |
| 2008/0183098 A1 | 7/2008 | Denison et al. |
| 2008/0188757 A1 | 8/2008 | Rovira et al. |
| 2008/0200802 A1 | 8/2008 | Bhavaraju et al. |
| 2008/0205717 A1 | 8/2008 | Reeves et al. |
| 2008/0221411 A1 | 9/2008 | Hausmann et al. |
| 2008/0247502 A1 | 10/2008 | Liao |
| 2008/0252304 A1 | 10/2008 | Woo et al. |
| 2008/0262375 A1 | 10/2008 | Brown et al. |
| 2008/0270051 A1 | 10/2008 | Essex et al. |
| 2008/0287823 A1 | 11/2008 | Chetham |
| 2008/0306400 A1 | 12/2008 | Takehara |
| 2008/0306402 A1 | 12/2008 | Singer |
| 2008/0319336 A1 | 12/2008 | Ward et al. |
| 2009/0018432 A1 | 1/2009 | He |
| 2009/0043222 A1 | 2/2009 | Chetham |
| 2009/0054952 A1 | 2/2009 | Glukhovsky et al. |
| 2009/0069708 A1 | 3/2009 | Hatlestad et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0076410 A1 | 3/2009 | Libbus et al. |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0105555 A1 | 4/2009 | Dacso et al. |
| 2009/0143663 A1* | 6/2009 | Chetham .................. A61B 5/053 600/372 |
| 2009/0177099 A1 | 7/2009 | Smith et al. |
| 2009/0209828 A1 | 8/2009 | Musin |
| 2009/0209872 A1 | 8/2009 | Pop |
| 2009/0216140 A1 | 8/2009 | Skrabal |
| 2009/0216148 A1 | 8/2009 | Freed et al. |
| 2009/0234244 A1 | 9/2009 | Tanaka |
| 2009/0240163 A1 | 9/2009 | Webler |
| 2009/0264727 A1 | 10/2009 | Markowitz |
| 2009/0264745 A1 | 10/2009 | Markowitz et al. |
| 2009/0264776 A1 | 10/2009 | Vardy |
| 2009/0264791 A1 | 10/2009 | Gregory et al. |
| 2009/0275854 A1 | 11/2009 | Zielinski et al. |
| 2009/0275855 A1 | 11/2009 | Zielinski et al. |
| 2009/0287102 A1 | 11/2009 | Ward |
| 2009/0306535 A1 | 12/2009 | Davies et al. |
| 2009/0318778 A1 | 12/2009 | Dacso et al. |
| 2009/0326408 A1 | 12/2009 | Moon |

(56) References Cited

U.S. PATENT DOCUMENTS

| | | |
|---|---|---|
| 2010/0007357 A1 | 1/2010 | Ammari et al. |
| 2010/0049077 A1 | 2/2010 | Sadleir et al. |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0100146 A1 | 4/2010 | Blomqvist |
| 2010/0106046 A1 | 4/2010 | Shochat et al. |
| 2010/0152605 A1 | 6/2010 | Ward |
| 2010/0168530 A1 | 7/2010 | Chetham et al. |
| 2010/0191141 A1 | 7/2010 | Aberg |
| 2010/0228143 A1 | 9/2010 | Teschner et al. |
| 2011/0025348 A1 | 2/2011 | Chetham et al. |
| 2011/0034806 A1 | 2/2011 | Hartov et al. |
| 2011/0046505 A1 | 2/2011 | Cornish et al. |
| 2011/0054343 A1 | 3/2011 | Chetham et al. |
| 2011/0054344 A1 | 3/2011 | Slizynski |
| 2011/0060239 A1 | 3/2011 | Gaw |
| 2011/0060241 A1 | 3/2011 | Martinsen et al. |
| 2011/0082383 A1 | 4/2011 | Cory et al. |
| 2011/0087129 A1 | 4/2011 | Chetham et al. |
| 2011/0118619 A1 | 5/2011 | Burton et al. |
| 2011/0190655 A1 | 8/2011 | Moissl et al. |
| 2011/0208084 A1 | 8/2011 | Martinez et al. |
| 2011/0230784 A2 | 9/2011 | Slizynski et al. |
| 2011/0245712 A1 | 10/2011 | Patterson et al. |
| 2011/0251513 A1 | 10/2011 | Chetham |
| 2011/0274327 A1 | 11/2011 | Wehnes et al. |
| 2011/0282180 A1 | 11/2011 | Goldkuhl et al. |
| 2012/0071772 A1 | 3/2012 | Chetham |
| 2012/0165884 A1 | 6/2012 | Xi |
| 2012/0238896 A1 | 9/2012 | Garber et al. |
| 2013/0102873 A1 | 4/2013 | Hamaguchi |
| 2013/0165760 A1 | 6/2013 | Erlinger et al. |
| 2013/0165761 A1 | 6/2013 | De Limon et al. |
| 2014/0148721 A1 | 5/2014 | Erlinger et al. |

FOREIGN PATENT DOCUMENTS

| | | | |
|---|---|---|---|
| CA | 2613524 | 1/2007 | |
| CA | 2615845 | 1/2007 | |
| CA | WO 2008119166 A1 * | 10/2008 | ............... H03F 1/14 |
| CN | 1180513 | 5/1998 | |
| CN | 1236597 | 12/1999 | |
| CN | 1329875 | 1/2002 | |
| DE | 2912349 | 10/1980 | |
| EP | 0249823 | 12/1987 | |
| EP | 349043 | 3/1990 | |
| EP | 0357309 | 3/1990 | |
| EP | 377887 | 7/1990 | |
| EP | 581073 | 2/1994 | |
| EP | 339471 | 3/1997 | |
| EP | 865763 | 9/1998 | |
| EP | 0869360 | 10/1998 | |
| EP | 1078597 | 2/2001 | |
| EP | 1080686 | 3/2001 | |
| EP | 1112715 | 4/2001 | |
| EP | 1112715 | 7/2001 | |
| EP | 1146344 | 10/2001 | |
| EP | 1114610 | 11/2001 | |
| EP | 1177760 | 2/2002 | |
| EP | 1219937 | 7/2002 | |
| EP | 1238630 | 9/2002 | |
| EP | 1247487 | 10/2002 | |
| EP | 1329190 | 7/2003 | |
| EP | 1338246 | 8/2003 | |
| EP | 1080686 | 3/2004 | |
| EP | 1452131 | 9/2004 | |
| EP | 1553871 | 7/2005 | |
| EP | 1118308 | 11/2005 | |
| EP | 1629772 | 3/2006 | |
| EP | 1247487 | 1/2008 | |
| EP | 1903938 | 4/2008 | |
| EP | 1909642 | 4/2008 | |
| EP | 1948017 | 7/2008 | |
| EP | 1353595 | 8/2008 | |
| FR | 2486386 | 1/1982 |
| FR | 2748928 | 11/1997 |
| GB | 1441622 | 7/1976 |
| GB | 2131558 | 6/1984 |
| GB | 2260416 | 4/1993 |
| GB | 2426824 | 12/2006 |
| JP | 6-74103 | 10/1994 |
| JP | 8191808 | 7/1996 |
| JP | 09051884 | 2/1997 |
| JP | 9220209 | 8/1997 |
| JP | 10000185 | 1/1998 |
| JP | 10014898 | 1/1998 |
| JP | 10014899 | 2/1998 |
| JP | 10225521 | 8/1998 |
| JP | 11070090 | 3/1999 |
| JP | 11-513592 | 11/1999 |
| JP | 2000107138 | 4/2000 |
| JP | 2000139867 | 5/2000 |
| JP | 2001037735 | 2/2001 |
| JP | 2001061804 | 3/2001 |
| JP | 2001-204707 | 7/2001 |
| JP | 2001224568 | 8/2001 |
| JP | 2001-245866 | 9/2001 |
| JP | 2001321352 | 11/2001 |
| JP | 2002502274 | 1/2002 |
| JP | 2002238870 | 8/2002 |
| JP | 2002330938 | 11/2002 |
| JP | 2002350477 | 12/2002 |
| JP | 2003-502092 | 1/2003 |
| JP | 2003075487 | 3/2003 |
| JP | 2003-116803 | 4/2003 |
| JP | 2003116805 | 4/2003 |
| JP | 2003230547 | 8/2003 |
| JP | 200461251 | 2/2004 |
| JP | 2006-501892 | 1/2006 |
| JP | 2008-502382 | 1/2008 |
| JP | 2008022995 | 7/2008 |
| JP | 2010-526604 | 8/2010 |
| RU | 2112416 | 6/1998 |
| WO | WO 88-07392 | 10/1988 |
| WO | WO 91-19454 | 12/1991 |
| WO | WO 93-18821 | 9/1993 |
| WO | WO 94/01040 | 1/1994 |
| WO | WO 94-10922 | 5/1994 |
| WO | WO 96-01586 | 1/1996 |
| WO | WO 96-12439 | 5/1996 |
| WO | WO 96-32652 | 10/1996 |
| WO | WO 97-11638 | 4/1997 |
| WO | WO 97-14358 | 4/1997 |
| WO | WO 97-24156 | 7/1997 |
| WO | WO 98-06328 | 2/1998 |
| WO | WO 98/12983 | 4/1998 |
| WO | WO 98-23204 | 6/1998 |
| WO | WO 98-33553 | 8/1998 |
| WO | WO 98-51211 | 11/1998 |
| WO | WO 99-42034 | 8/1999 |
| WO | WO 99-48422 | 9/1999 |
| WO | WO 00-19886 | 4/2000 |
| WO | WO 00-40955 | 7/2000 |
| WO | WO 00-78213 | 12/2000 |
| WO | WO 00-79255 | 12/2000 |
| WO | WO 01-27605 | 4/2001 |
| WO | WO 01-50954 | 7/2001 |
| WO | WO 01-52733 | 7/2001 |
| WO | WO 01-67098 | 9/2001 |
| WO | WO 02-053028 | 7/2002 |
| WO | WO 02-062214 | 8/2002 |
| WO | WO 02-094096 | 11/2002 |
| WO | WO 04-000115 | 12/2003 |
| WO | WO 2004/002301 | 1/2004 |
| WO | WO 2004/006660 | 1/2004 |
| WO | WO 2004-021880 | 3/2004 |
| WO | WO 2004-026136 | 4/2004 |
| WO | WO 2004-030535 | 4/2004 |
| WO | WO 2004-032738 | 4/2004 |
| WO | WO 2004-043252 | 5/2004 |
| WO | WO 2004-047635 | 6/2004 |
| WO | WO 2004-047636 | 6/2004 |
| WO | WO 2004-047638 | 6/2004 |

(56) References Cited

FOREIGN PATENT DOCUMENTS

| | | |
|---|---|---|
| WO | WO 2004-049936 | 6/2004 |
| WO | WO 2004-083804 | 9/2004 |
| WO | WO 2004-084087 | 9/2004 |
| WO | WO 2004-084723 | 10/2004 |
| WO | WO 2004-098389 | 11/2004 |
| WO | WO 2004/112563 | 12/2004 |
| WO | WO 2005-010640 | 2/2005 |
| WO | WO 2005-018432 | 3/2005 |
| WO | WO 2005-027717 | 3/2005 |
| WO | WO 2005-051163 | 6/2005 |
| WO | WO 2005-051194 | 6/2005 |
| WO | WO 2005-122881 | 12/2005 |
| WO | WO 2005-122888 | 12/2005 |
| WO | WO 2006-045051 | 4/2006 |
| WO | WO 2006-056074 | 6/2006 |
| WO | WO 2006-129108 | 12/2006 |
| WO | WO 2006-129116 | 12/2006 |
| WO | WO 2007-002991 | 1/2007 |
| WO | WO 2007-002992 | 1/2007 |
| WO | WO 2007-002993 | 1/2007 |
| WO | WO 2007-009183 | 1/2007 |
| WO | WO 2007-041783 | 4/2007 |
| WO | WO 2007/045006 | 4/2007 |
| WO | WO 2007-056493 | 5/2007 |
| WO | WO 2007-070997 | 6/2007 |
| WO | WO 2007/105996 | 9/2007 |
| WO | WO 2007-128952 | 11/2007 |
| WO | WO 2008-011716 | 1/2008 |
| WO | WO 2008-054426 | 8/2008 |
| WO | WO 2008/119166 | 10/2008 |
| WO | WO 2008-138062 | 11/2008 |
| WO | WO 2008/149125 | 12/2008 |
| WO | WO 2009-018620 | 2/2009 |
| WO | WO 2009-027812 | 3/2009 |
| WO | WO 2009-036369 | 3/2009 |
| WO | WO 2009-068961 | 6/2009 |
| WO | WO 2009/100491 | 8/2009 |
| WO | WO 2009-112965 | 9/2009 |
| WO | WO 2010-003162 | 1/2010 |
| WO | WO 2010-029465 | 3/2010 |
| WO | WO 2010-069023 | 6/2010 |
| WO | WO 2010-076719 | 7/2010 |
| WO | WO 2011-018744 | 2/2011 |
| WO | WO 2011-022068 | 2/2011 |
| WO | WO 2011-050093 | 5/2011 |
| WO | WO 2011-075769 | 6/2011 |
| WO | WO 2011-113169 | 9/2011 |
| WO | WO 2011-136867 | 11/2011 |

OTHER PUBLICATIONS

Al-Hatib, F.; Patient Instrument connection errors in bioelectrical impedance measurement; Physiological Measurement; vol. 19, No. 2, pp. 285-296; May 2, 1998.

Bella, et al., Relations of Left Ventricular Mass to Fat-Free and Adipose Body Mass: The Strong Heart Study, (1998) Circulation, vol. 98, pp. 2538-2544.

Boulier, A. et al.; Fat-Free Mass Estimation by Two Electrode Impedance Method; American Journal of Clinical Nutrition; vol. 52, pp. 581-585; 1990.

Bracco, D. et al., Bedside determination of fluid accumulation after cardiac surgery using segmental bioelectrical impedance, Critical Care Medicine, vol. 26, No. 6, pp. 1065-1070, 1998.

Chaudary, S.S. et al.; Dielectric Properties of Normal & Malignant Human Breast Tissues at Radiowave and Microwave Frequencies; Indian Journal of Biochemistry & Biophysics; vol. 21, No. 1, pp. 76-79; 1984.

Chiolero, R.L. et al.; Assessment of changes in body water by bioimpedance in acutely ill surgical patients; Intensive Care Medicine; vol. 18, pp. 322-326; 1992.

Chumlea et al.; Bioelectrical Impedance and Body Composition: Present Status and Future Directions; Nutrition Reviews; vol. 52, No. 4, pp. 123-131; 1994.

Cornish, B.H. et al.; Alteration of the extracellular and total body water volumes measured by multiple frequency bioelectrical impedance analysis; Nutrition Research; vol. 14, No. 5, pp. 717-727; 1994.

Cornish, B.H. et al.; Bioelectrical impedance for monitoring the efficacy of lymphoedema treatment programmes; Breast Cancer Research and Treatment; vol. 38, pp. 169-176; 1996.

Cornish, B.H. et al.; Data analysis in multiple-frequency bioelectrical impedance analysis; Physiological Measurement; vol. 19, No. 2, pp. 275-283; May 1, 1998.

Cornish, B.H. et al.; Early diagnosis of lymphedema using multiple frequency bioimpedance; Lymphology; vol. 34, pp. 2-11; Mar. 2001.

Cornish, B.H. et al.; Early diagnosis of lymphoedema in postsurgery breast cancer patients; Annals New York Academy of Sciences; pp. 571-575; May 2000.

Cornish, B.H. et al.; Quantification of Lymphoedema using Multi-frequency Bioimpedance; Applied Radiation and Isotopes; vol. 49, No. 5/6, pp. 651-652; 1998.

De Luca, F. et al., Use of low-frequency electrical impedance measurements to determine phospoholipid content in amniotic fluid; Physics in Medicine and Biology, vol. 41, pp. 1863-1869, 1996.

Deurenberg, P. et al., Multi-frequency bioelectrical impedance: a comparison between the Cole-Cole modelling and Hanai equations with the classically impedance index approach, Annals of Human Biology, vol. 23, No. 1, pp. 31-40, 1996.

Dines K.A. et al.; Analysis of electrical conductivity imaging; Geophysics; vol. 46, No. 7, pp. 1025-1036; Jul. 1981.

Ellis, K.J. et al; Human hydrometry: comparison of multifrequency bioelectrical impedance with 2H2O and bromine dilution; Journal of Applied Physiology; vol. 85, No. 3, pp. 1056-1062; 1998.

Ezenwa, B.N. et al.; Multiple Frequency System for Body Composition Measurement; Proceedings of the Annual International Conference of the Engineering in Medicine and Biology Society; vol. 15; pp. 1020-1021; 1993.

Forslund, A.H. et al.; Evaluation of modified multicompartment models to calculate body composition in healthy males; American Journal of Clinical Nutrition; vol. 63, pp. 856-862; 1996.

Gersing, E.; Impedance spectroscopy on living tissue for determination of the state of Organs; Bioelectrochemistry and Bioenergetics; vol. 45, pp. 145-149; 1998.

Gerth, W.A. et al.; A computer-based bioelectrical impedance spectroscopic system for noninvasive assessment of compartmental fluid redistribution; Third Annual IEEE Symposium on Computer Based Medical Systems, Jun. 3-6, 1990, University of NC. At Chapel Hill; pp. 446-453; Jun. 1990.

Gudivaka R. et al; Single- and multifrequency models for bioelectrical impedance analysis of body water compartments; Applied Physiology; vol. 87, Issue 3, pp. 1087-1096; 1999.

Iacobellis, G., et al. Influence of Excess Fat on Cardiac Morphology and Function: Study in Uncomplicated Obesity, (2002) Obesity Research, vol. 10, pp. 767-773.

Ivorra, A., et al.; Bioimpedance Dispersion Width as a Parameter to Monitor Living Tissues; Physiological Measurement; vol. 26; pp. 1-9; 2005.

Jones, C.H. et al; Extracellular fluid volume determined by bioelectric impedance and serum albumin in CAPD patients; Nephrology Dialysis Transplantation; vol. 13, pp. 393-397; 1998.

Jossinet, J. et al.; A Study for Breast Imaging with a Circular Array of Impedance Electrodes; Proc. Vth Int. Conf. Bioelectrical Impedance, 1981, Tokyo, Japan; pp. 83-86; 1981.

Jossinet, J. et al.; Technical Implementation and Evaluation of a Bioelectrical Breast Scanner; Proc. 10.sup.th Int. Conf. IEEE Engng. Med. Biol., 1988, New Orleans, USA (Imped. Imaging II); vol. 1. p. 289; 1988.

Kanai, H. et al.; Electrical Measurement of Fluid Distribution in Legs and Arms; Medical Progress through technology; pp. 159-170; 1987.

Karason, K., et al., Impact of Blood Pressure and Insulin on the Relationship Between Body Fat and Left Ventricular Structure, (2003) European Heart Journal, vol. 24, pp. 1500-1505.

(56) References Cited

OTHER PUBLICATIONS

Kim, C.T. et al.; Bioelectrical impedance changes in regional extracellular fluid alterations; Electromyography and Clinical Neurophysiology; vol. 37, pp. 297-304; 1997.

Liu R. et al; Primary Multi-frequency Data Analyze in Electrical Impedance Scanning; Proceedings of the IEEE-EMBS 2005, 27th Annual International Conference of the Engineering in Medicine and Biology Society, Shanghai, China; pp. 1504-1507; , Sep. 1-4, 2005.

Lozano, A. et al.; Two-frequency impedance plethysmograph: real and imaginary parts; Medical & Biological Engineering & Computing; vol. 28, No. 1, pp. 38-42; Jan. 1990.

Lukaski, H.C. et al.; Estimation of Body Fluid Volumes Using Tetrapolar Bioelectrical Impedance Measurements; Aviation, Space, and Environmental Medicine; pp. 1163-1169; Dec. 1988.

Man, B. et al. Results of Preclinical Tests for Breast Cancer Detection by Dielectric Measurements; XII Int. Conf. Med. Biol. Engng. 1979, Jerusalem, Israel. Springer Int., Berlin; Section 30.4; 1980.

Mattar, J.A., Application of Total Body Impedance to the Critically Ill Patient, New Horizons, vol. 4, No. 4, pp. 493-503, Nov. 1996.

McCullah, et al.; Bioelectrical Impedance Analysis Measures the Ejection Fraction of the Calf Muscle Pump; IFMBE Proceedings; vol. 17, pp. 616-619; 2007.

McDougal D., et al.; Body Composition Measurements From Whole Body Resistance and Reactance; Surgical Forum; vol. 36, pp. 43-44; 1986.

Osterman K.S. et al.; Multifrequency electrical impedance imaging: preliminary in vivo experience in breast; Physiological Measurement; vol. 21, No. 1, pp. 99-109; Feb. 2000.

Ott, M. et al.; Bioelectrical Impedance Analysis as a Predictor of Survival in Patients with Human Immunodeficiency Virus Infection; Journal of Acquired Immune Deficiency Syndromes and Human Retrovirology; vol. 9, pp. 20-25; 1995.

Pethig, R. et al.; The Passive Electrical Properties of Biological Systems: Their Significance in Physiology, Biophysics and Biotechnology; Physics in Medicine and Biology; vol. 32, pp. 933-970; 1987.

Piperno, G. et al.; Breast Cancer Screening by Impedance Measurements; Frontiers of Medical & Biological Engineering; vol. 2, pp. 111-117; 1990.

Rigaud, B. et al.; Bioelectrical Impedance Techniques in Medicine; Critical Reviews in Biomedical Engineering; vol. 24 (4-6), pp. 257-351; 1996.

Scharfetter, H. et al.; Effect of Postural Changes on the Reliability of Volume Estimations from Bioimpedance Spectroscopy Data; Kidney International; vol. 51, No. 4, pp. 1078-2087; 1997.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; vol. 5, pp. 1934-1935; Oct. 31, 1996.

Skidmore, R. et al.; A Data Collection System for Gathering Electrical Impedance Measurements from the Human Breast; Clinical Physics Physiological Measurement; vol. 8, pp. 99-102; 1987.

Sollish, B.D. et al.; Microprocessor-assisted Screening Techniques; Israel Journal of Medical Sciences; vol. 17, pp. 859-864; 1981.

Steijaert, M. et al.; The use of multi-frequency impedance to determine total body water and extracellular water in obese and lean female individuals; International Journal of Obesity; vol. 21, pp. 930-934; 1997.

Surowiec, A.J. et al.; Dielectric Properties of Brest Carcinoma and the Surrounding Tissues; IEEE Transactions on Biomedical Engineering; vol. 35, pp. 257-263; 1988.

Tedner, B.; Equipment Using Impedance Technique for Automatic Recording of Fluid-Volume Changes During Haemodialysis; Medical & Biological Engineering & Computing; pp. 285-290; 1983.

Thomas. B.J. et al.; Bioelectrical impedance analysis for measurement of body fluid volumes—A review; Journal of Clinical Engineering; vol. 17, No. 16, pp. 505-510; 1992.

Thomas. B.J. et al.; Bioimpedance Spectrometry in Determination of Body Water Compartments: Accuracy and Clinical Significance; Applied Radiation and Isotopes; vol. 49, No. 5/6, pp. 447-455; 1998.

Thomas. B.J.; Future Technologies; Asia Pacific Journal Clinical Nutrition; vol. 4, pp. 157-159; 1995.

Ulgen, Y. et al.; Electrical parameters of human blood; Engineering in Medicine and Biology Society, 1998. Proceedings of the 20th Annual International Conference of the IEEE; vol. 6, pp. 2983-2986; Nov. 1, 1998.

Ward, L.C. et al., Multi-frequency bioelectrical impedance augments the diagnosis and management of lymphoedema in postmastectomy patients, European Journal of Clinical Investigation, vol. 22, pp. 751-754, 1992.

Ward, L.C. et al.; Determination of Cole parameters in multiple frequency bioelectrical impedance analysis using only the measurement of impedances; Four-frequency fitting; Physiological Measurement; vol. 27, No. 9, pp. 839-850; Sep. 2006.

Ward, L.C. et al.; There is a better way to measure Lymphoedema; National Lymphedema Network Newsletter; vol. 7, No. 4, pp. 89-92; Oct. 1995.

Woodrow, G. et al; Effects of icodextrin in automated peritoneal dialysis on blood pressure and bioelectrical impedance analysis; Nephrology Dialysis Transplantation; vol. 15, pp. 862-866; 2000.

Yamakoshi, K.; Non-Invasive Cardiovascular Hemodynamic Measurements; Sensors in Medicine and Health Care; pp. 107-160; 2004.

Yoshinaga, M., Effect of Total Adipose Weight and Systemic Hypertension on Left Ventricular Mass in Children, American Journal of Cardiology, (1995) vol. 76, pp. 785-787.

International Search Report and Written Opinion of the International Searching Authority issued in PCT/AU2006/000922 dated Oct. 10, 2006.

International Search Report and Written Opinion of the International Searching Authority issued in PCT/AU2008/000588 dated Aug. 13, 2008.

International Search Report from International Application No. PCT/AU2006/000924 dated Sep. 27, 2006.

Cornish, et al., "Optimizing Electrode Sites for Segmental Bioimpedance Measurements" Physiological Measurement, Institute of Physics, 1999, pp. 241-250, vol. 20, No. 3.

Cornish, et al., "A New Technique for the Quantification of Peripheral Edema with Application in Both Unilateral and Bilateral Cases" Angiology, 2002, pp. 41-47, vol. 53, No. 1.

Fenech, et al., "Extracellular and Intracellular Volume Variations During Postural Change Measured by Segmental and Wrist-Ankle Bioimpedance Spectroscopy" IEEE Transactions on Biomedical Engineering, IEEE Service Center, 2004, pp. 166-175, vol. 51, No. 1.

Golden, et al., "Assessment of Peripheral Hemodynmics using Impedance Plethysmogrphy" Physical Therapy, 1986, pp. 1544-1547, vol. 66, No. 10.

Kim, et al., "Impedance Tomography and its Application in Deep Venous Thrombosis Detection" IEEE Engineering in Medicine and Biology Magazine, IEEE Service Center, 1989, pp. 46-49, vol. 8, No. 1.

Nawarycz, et al., "Triple-frequency Electroimpedance Method for Evaluation of Body Water Compartments" Medical & Biological Engineering & Computing, 1996, pp. 181-182, vol. 34, No. Supp. 01, Pt. 02.

Noshiro, et al., "Electrical Impedance in the Lower Limbs of Patients with Duchenne Muscular Dystrophy: A Preliminary Study" Medical & Biological Engineering & Computing, 1993, pp. 97-102, vol. 31, No. 2.

Seo, et al., "Measuring Lower Leg Swelling: Optimum Frequency for Impedance Method" Medical & Biological Engineering & Computing, 2001, pp. 185-189, vol. 39.

Seoane, et al., "Current Source for Wideband Electrical Bioimpedance Spectroscopy Based on a Single Operational Amplifier" World Congress on Medical Physics and Biomedical Engineering 2006, pp. 707-710, vol. 14.

Smith, et al., "A Pilot Study for Tissue Characterization Using Bio-impedance Mapping" 13th International Conference on Elec-

(56) References Cited

OTHER PUBLICATIONS trical Bio-impedance and the 8th Conference on Electrical Impedance Tomography 2007, pp. 146-149.
Stanton, et al., "Non-invasive Assessment of the Lymphedematous Limb" Lymphology, The International Society of Lymphology, 2000, pp. 122-135, vol. 33, No. 3.
Bernstein; A New Stroke Volume Equation for Thoracic Electrical Bio Impedance; Critical Care Medicine; vol. 14, pp. 904-909; 1986.
Blad et al.; Impedance Spectra of Tumour Tissue in Tomparison with Normal Tissue; A Possible Clinical Application for Electrical Impedance Tomography; Physiological Measurement; vol. 17, pp. A105-A115; 1996.
De Lorenzo et al.; Determination of Intracellular Water by Multifrequency Bioelectrical Impedance; Ann. Nutr. Metab.; vol. 39, pp. 177-184; 1995.
Edwards, L.S.; A Modified Pseudosection for Resistivity and IP; Geophysics; vol. 42, No. 5, pp. 1020-1036; 1977.
Hansen, E.; On the Influence of Shape and Variations in Conductivity of the Sample on Four-Point Measurements; Applied Scientific Research; Section B; vol. 8, Issue 1, pp. 93-104 1960.
Igel, J.; On the Small-Scale Variability of Electrical Soil Properties and Its Influence on Geophysical Measurements; Ph.D. Thesis; Frankfurt University; Hanover, Germany; p. 188; 2007.
Kyle et al.; Bioelectrical Impedance Analysis—Part I: Review of Principles and Methods; Clinical Nutrition; vol. 23, pp. 1226-1243; 2004.
Loke et al.; Least Squares Deconvolution of Apparent Resistivity Pseudosections; Geophysics; vol. 60, No. 6, pp. 1682-1690; 1995.
McAdams et al; Tissue Impedance: a Historical Overview Physiological Measurement; Institute of Physics Publishing; vol. 16. (3A), pp. A1-A13; 1995.

McEwan et al.; Battery Powered and Wireless Electrical Impedance Tomography Spectroscopy Imaging Ssing Bluetooth; Medicon IFMBE Proceedings; vol. 16, pp. 798-801; 2007.
Roy, A.; Depth of investigation in Direct Current Methods Geophysics; vol. 36, pp. 943-959; 1971.
Wilson et al.; Feasibility Studies of Electrical Impedance Spectroscopy for Monitoring Tissue Response to Photodynamic Therapy; Optical Methods for Tumor Treatment and Detections: Mechanisms and Techniques in Photodynamic Therapy VII; Proc. SPIE 3247; pp. 69-80; 1998.
International Search Report and Written Opinion of the International Searching Authority issued in PCT/AU2009/000163 dated Apr. 16, 2009.
International Search Report and Written Opinion of the International Searching Authority issued in PCT/AU2006/000922 dated Oct. 13, 2006.
International Search Report and Written Opinion of the International Searching Authority issued in PCT/AU2006/001057 dated Oct. 25, 2006.
International Search Report and Written Opinion of the International Searching Authority issued in PCT/AU2008/000034 dated Mar. 17, 2008.
International Search Report and Written Opinion of the International Searching Authority issued in PCT/CA2008/000588 dated Aug. 13, 2008.
International Search Report and Written Opinion of the International Searching Authority issued in PCT/AU2006/000924 dated Oct. 5, 2006.
International Search Report and Written Opinion of the International Searching Authority issued in PCT/AU2008/001521 dated Jan. 15, 2009.

* cited by examiner

SIGNAL DISTRIBUTION FOR PATIENT-ELECTRODE MEASUREMENTS

RELATED APPLICATIONS

This application is a U.S. National Phase under 35 U.S.C. §371 of the International Patent Application No. PCT/AU2010/001552, filed Nov. 18, 2010, and published in English on May 5, 2011 as WO 2011/060497, which claims the benefit of Australian Patent Application No. 2009905642, filed Nov. 18, 2009, both of which are incorporated by reference in their entirety.

The section headings used herein are for organizational purposes only and are not to be construed as limiting the subject matter described in any way.

BACKGROUND OF THE INVENTION

The present invention relates to apparatus for electrically connecting measurement apparatus to a biological subject, and in particular, to a circuit for electrical impedance measurements, which in one example allows drive signal injection and signal amplitude and phase measurement.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological indicators relating to a subject, such as cardiac function, body composition, and other health status indicators, such as the presence of oedema, involves the use of bioelectrical impedance. This process typically involves using a measuring device to measure the electrical impedance of a subject's body using a series of electrodes placed on the skin surface. Changes in electrical impedance measured at the body's surface are used to determine parameters, such as changes in fluid levels, associated with the cardiac cycle, oedema, or the like.

Impedance measuring apparatus is sometimes sensitive to external factors, including stray capacitances between the subject and the local environment and the measurement apparatus, variations in electrode/tissue interface impedances, also known as electrode impedances, as well as stray capacitances and inductive coupling between the leads used to connect the measuring device to the electrodes.

It will be appreciated that similar issue also arise when making other electrical measurements relating to biological subjects.

WO2009/059351 describes apparatus for use in performing impedance measurements on a subject. The apparatus includes a processing system for causing a first signal to be applied to the subject, determining an indication of a second signal measured across the subject, using the indication of the second signal to determine any imbalance and if an imbalance exists, determining a modified first signal in accordance with the imbalance and causing the modified first signal to be applied to the subject to thereby allow at least one impedance measurement to be performed.

SUMMARY OF THE PRESENT INVENTION

In a first broad form the present invention provides apparatus for electrically connecting measurement apparatus to a biological subject, the apparatus including a signal delivery circuit including:
 a) a current buffer having:
  i) a current buffer input for receiving a signal from a signal source; and,
  ii) a current buffer output for supplying a current to an electrode attached to the biological subject; and,
 b) a voltage buffer having:
  i) a voltage buffer input coupled to the current buffer output; and,
  ii) a voltage buffer output for providing a voltage signal indicative of a voltage at the electrode, to a sensor.

Typically the current buffer is a current conveyor.

Typically the voltage buffer is an amplifier connected as an output follower.

Typically the apparatus includes an offset control circuit coupled between the voltage buffer output and the current buffer input.

Typically the offset control circuit includes an integrator coupled between the voltage buffer output and the current buffer input.

Typically the offset control circuit is used to control a DC offset at the electrode.

Typically the signal delivery circuit includes a negative impedance circuit coupled between the voltage buffer output and the current buffer output.

Typically the negative impedance circuit includes a negative impedance circuit amplifier and a compensation impedance.

Typically at least one of a gain of the negative impedance circuit amplifier and a value of the compensation impedance is selected to compensate for parasitic impedance losses.

Typically the negative impedance circuit includes:
 a) a compensation impedance having a compensation impedance value, a first terminal and a second terminal, the first terminal coupled to the current buffer output; and,
 b) a compensation amplifier having a compensation amplifier input, a compensation amplifier output and a gain, the compensation amplifier input coupled to the voltage buffer output, the compensation amplifier output coupled to the second terminal of the compensation impedance to provide a compensation current to flow through the impedance, and the gain and the compensation impedance values are selected based on the parasitic impedance value so that the compensation current has a magnitude substantially equal to the leakage current magnitude.

Typically the apparatus includes:
 a) a plurality of signal delivery circuits, each signal delivery circuit being for supplying a current to a respective electrode attached to the biological subject;
 b) at least one signal source; and,
 c) at least one first multiplexer for selectively connecting the signal source to one of the plurality of signal delivery circuits to thereby apply a current to the biological circuit via the respective electrode.

Typically the apparatus includes:
 a) a plurality of signal delivery circuits, each signal delivery circuit being for providing a voltage signal indicative of a voltage at the electrode, to a sensor;
 b) at least one sensor; and, c) at least one second multiplexer for selectively connecting the at least one sensor to one of the plurality of signal delivery circuits to thereby allow the sensor to sense the voltage signal indicative of a voltage at the respective electrode.

Typically the apparatus includes, first and second signal sources for generating respective first and second drive signals, the first and second signal sources being coupled to respective signal delivery circuits.

Typically the first and second signal sources are for generating at least one of:
a) complementary signals;
b) signals having a constant amplitude and phase; and,
c) signals having a controlled amplitude and phase.

Typically at least one signal source is coupled to ground.

Typically the apparatus includes:
a) at least one signal delivery circuit for supplying a current to a drive electrode attached to the biological subject; and,
b) at least one signal delivery circuit for providing a voltage signal indicative of a voltage at a sense electrode.

Typically the measurement apparatus includes at least one signal source and at least one sensor.

Typically the measurement apparatus is an impedance measurement apparatus.

In a second broad form the present invention provides a current multiplexing system comprising:
a) a plurality of current multiplexers having at least one input and a plurality of outputs;
b) a first and second alternating-current current source each current source having a constant magnitude and frequency, wherein the second current source is complimentary to the first current source, each of the first and second current sources is coupled to an input of a current multiplexer;
c) a plurality of current delivery circuits, each current delivery circuit having an input, a current output and a voltage output, wherein each current delivery circuit input is coupled to an output of a current multiplexer;
d) a plurality of electrodes, each of the plurality of electrodes being coupled to a current output of one of the plurality of current delivery circuits; and
e) at least one voltage multiplexer having a plurality of inputs and at least one output;
f) wherein each current delivery circuit comprises:
i) a current conveyor, having an input and an output, the current conveyor input being coupled to the current delivery circuit input and the current conveyor output being coupled to the current delivery circuit current output;
ii) a voltage buffer, having an input and an output, the voltage buffer input being coupled to the current delivery circuit current output and the voltage buffer output being coupled to the current delivery circuit voltage output;
iii) an integrator coupled between the voltage buffer output and the current conveyor input; and,
iv) a negative impedance circuit coupled between the voltage buffer output and the current conveyor output, the negative impedance comprising:
(1) a compensation impedance having a compensation impedance value, a first terminal and a second terminal, the first terminal coupled to the current conveyor output;
(2) a compensation amplifier having a compensation amplifier input, a compensation amplifier output and a gain, the compensation amplifier input coupled to the voltage buffer output, the compensation amplifier output coupled to the second terminal of the compensation impedance to provide a compensation current to flow through the impedance, and the gain and the compensation impedance values are selected based on the parasitic impedance value so that the compensation current has a magnitude substantially equal to the leakage current magnitude.

In a third broad form the present invention provides apparatus for electrically connecting measurement apparatus to a biological subject, the apparatus including a signal delivery circuit including:
a) a first buffer having:
i) a first buffer input for receiving a signal from a signal source; and,
ii) a first buffer output for supplying a drive signal to an electrode attached to the biological subject; and,
b) a second buffer having:
i) a second buffer input coupled to the first buffer output; and,
ii) a second buffer output for providing a sensed signal indicative of a signal at the electrode, to a sensor.

Typically the first buffer is a current buffer, the drive signal being a drive current.

Typically the current buffer is a current conveyor.

Typically the second buffer is a voltage buffer the sensed signal being a voltage signal indicative of a voltage at the electrode.

Typically the second buffer is a current buffer the sensed signal being indicative of the drive current.

In a fourth broad form the present invention provides apparatus for use in performing impedance measurements on a subject, wherein the apparatus includes:
a) a signal source for applying a signal to a subject;
b) a sensor for sensing signals from the subject;
c) a processing system for controlling the signal source and receiving signals from the sensor; and,
d) at least one signal delivery circuit, including:
i) a first buffer having:
(1) a first buffer input for receiving a signal from a signal source; and,
(2) a first buffer output for supplying a drive signal to an electrode attached to the biological subject; and,
ii) a second buffer having:
(1) a second buffer input coupled to the first buffer output; and,
(2) a second buffer output for providing a sensed signal indicative of a signal at the electrode, to a sensor.

Typically the apparatus includes:
a) at least one signal delivery circuit for supplying a current to a drive electrode attached to the biological subject; and,
b) at least one signal delivery circuit for providing a voltage signal indicative of a voltage at a sense electrode.

Typically the apparatus includes:
a) a first signal delivery circuit coupled to a drive electrode attached to the biological subject, the first signal delivery circuit including:
i) a first buffer having:
(1) a first buffer input for receiving a signal from the signal source; and, (2) a first buffer output for supplying the drive signal to the drive electrode; and, ii) a second buffer having:

(1) a second buffer input coupled to the first buffer output; and, (2) a second buffer output for providing a sensed signal indicative of the drive signal at the drive electrode;

b) a second signal delivery circuit coupled to a sense electrode attached to the biological subject, the second signal delivery circuit including, i) a first buffer having:

(1) a first buffer input coupled to ground; and, (2) a first buffer output coupled to the sense electrode; and, ii) a second buffer having:

(1) a second buffer input coupled to the first buffer output; and, (2) a second buffer output for providing a sensed signal indicative of a sensed voltage at the sense electrode.

BRIEF DESCRIPTION OF THE DRAWINGS

The skilled person in the art will understand that the drawings, described below, are for illustration purposes only. The drawings are not intended to limit the scope of the applicants' teachings in any way.

An example of the present invention will now be described with reference to the accompanying drawings, in which.

DETAILED DESCRIPTION OF THE PREFERRED EMBODIMENTS

Electronic testing equipment or measuring apparatus may be electrically connected with a test subject through electrodes. These electrodes may be used to, for example, deliver currents and measure voltages at various points of contact between the test subject and the electrodes. An example of such test equipment or measuring apparatus can include medical equipment, in which case the test subject can be a biological subject such as a human patient.

Figure 1:
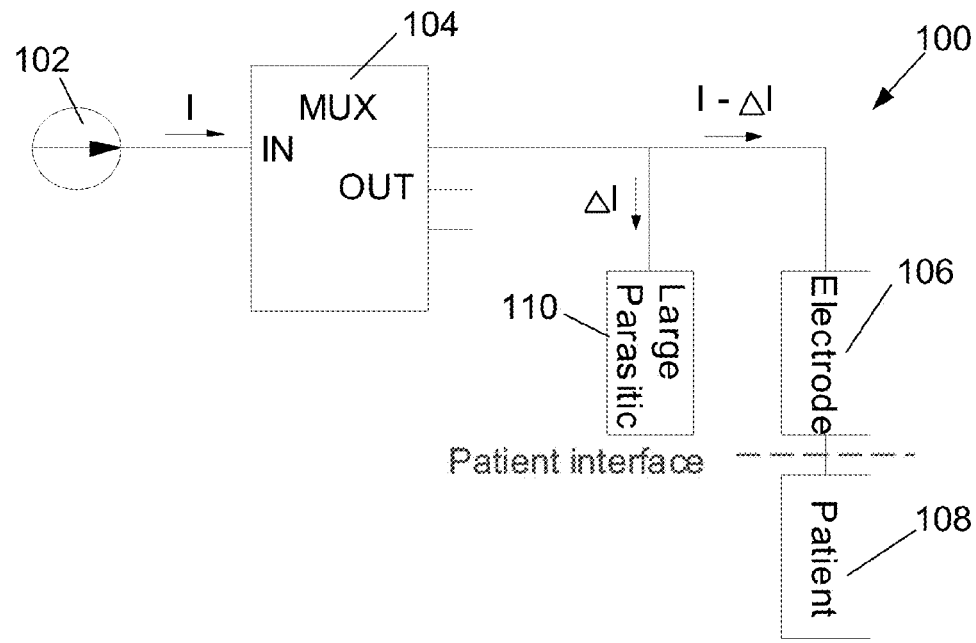
FIG. 1 is a schematic diagram of a current multiplexing system.

Regardless of the type of application, a signal source, such as a current source may be used to deliver a drive signal, such as a current, to the electrodes. Often a single current source may be used for multiple electrodes by switching the currents to the various electrodes as needed. FIG. 1 illustrates a current multiplexing system 100. Current multiplexing system 100 comprises a current source 102 coupled to the input of multiplexer 104. Each of the outputs of multiplexer 104 can in turn be coupled to a plurality of electrodes 106. For clarity FIG. 1, only illustrates a single electrode. Each of electrodes 106 can be coupled to a patient 108.

Current source 102 is used to deliver a current I to the input of multiplexer 104. Multiplexer 104 is then used to switch the input current to a particular output and thereby to a particular electrode 106. However, multiplexer 104 can cause a large parasitic impedance 110 to appear at each of the outputs. Consequently, some of the current outputted by multiplexer 104 is lost to parasitic impedance 110 as a leakage current (ΔI). Therefore, only a portion (I-ΔI) of the current produced by current source 102 reaches the electrode 106. The amount of current lost is proportional to the impedance of the interface between electrode 106 and patient 108. Each individual patient may have a different impedance associated with their skin and/or tissue. Consequently, the proportion of the total current that is lost to parasitic impedance 110 may differ with each individual patient. Accordingly, the proportion of total current delivered to the patient may also differ with each individual patient. Thus, with current multiplexing system 100 it can be difficult to deliver a precise amount of current to a patient 108 via an electrode 106.

Figure 2:
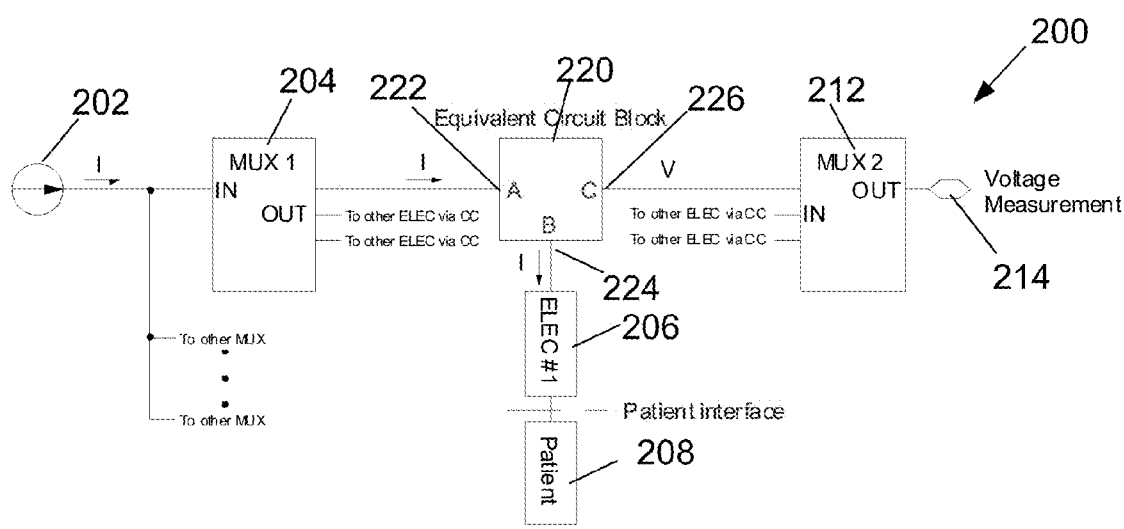
FIG. 2 is a schematic diagram of a current multiplexing system according to various embodiments of applicants' teachings.

Reference is now made to FIG. 2, which illustrates various embodiments of current multiplexing system 200, according to various embodiments of applicants' teachings. Current multiplexing system 200 comprises a current source 202, one or more multiplexers 204, a plurality of electrodes 206 coupled to patient 208, one or more voltage multiplexers 212, and a plurality of current delivery circuits 220. Node 214, which is the output of multiplexer 212, can be used to obtain voltage measurements.

Each output of each multiplexer 204 can be connected to a current delivery circuit similar to current delivery circuit 220, which in turn can be connected to the inputs of multiplexer 212. For clarity, FIG. 2 only illustrates a single connection to the output of multiplexer 204 and a single connection to multiplexer 212. The actual number of multiplexers 204, current delivery circuits 220, and multiplexers 212 used depends on such factors as the number electrodes 206 that are coupled to the patient, the number of outputs available on each multiplexer 204, and the number of inputs available on multiplexer 212.

In various embodiments according to applicants teachings, current delivery circuit 220 receives a current I at node 222 and outputs a substantially equal current at node 224. In addition, in various embodiments, current delivery circuit 220 produces a voltage at node 226 that is substantially equal to the voltage at node 224. As was explained above, node 226 is coupled to voltage multiplexer 212. However, it should be understood that voltage measurements can be taken directly at node 226, which is the voltage output of delivery circuit 220. The use of voltage multiplexer 212 is optional and can be used to reduce the number of nodes to which voltage measurement equipment is to be connected to.

As will be described in greater detail herein, in various embodiments, current multiplexing system 200 can utilize a single controlled constant current source 202 to deliver a current that is multiplexed to numerous electrical loads, such as electrodes 206. In some embodiments, constant current source 202 delivers an AC current with a constant amplitude and phase, which may for example be, but not limited to, a sinusoid of fixed frequency.

In some embodiments, current multiplexing system 200 can deliver a current to a load that is substantially equal to the current outputted by 202. In various embodiments, current multiplexing system 200 can be utilized to deliver a controllable constant current to numerous locations and loads with a small transmission loss. In addition, in various embodiments, current multiplexing system 200 can be used without a calibration step prior to use. Furthermore, in various embodiments, the loads to which current multiplexing system 200 connects need not be altered in any manner in order to utilize current multiplexing system 200. In some embodiments, current delivery circuit 200 can be utilized with any appropriate equipment including but not limited to measuring apparatus such as medical instrumentation, biometric instrumentation, electrocardiograph equipment, impedance measuring apparatus, and circuit testing equipment.

In various embodiments, current delivery circuit 220 can be integrated on a single integrated circuit. In some embodiments, a plurality of current delivery circuit, such as delivery circuit 220 can be integrated on a single integrated circuit and packaged in a single chip. In some embodiments, one or more current multiplexers, such as multiplexer 204, a plurality of delivery circuits and one or more voltage multiplexers, such as multiplexer 212, can be integrated on a single integrated circuit and packaged in a single chip.

Figure 3:
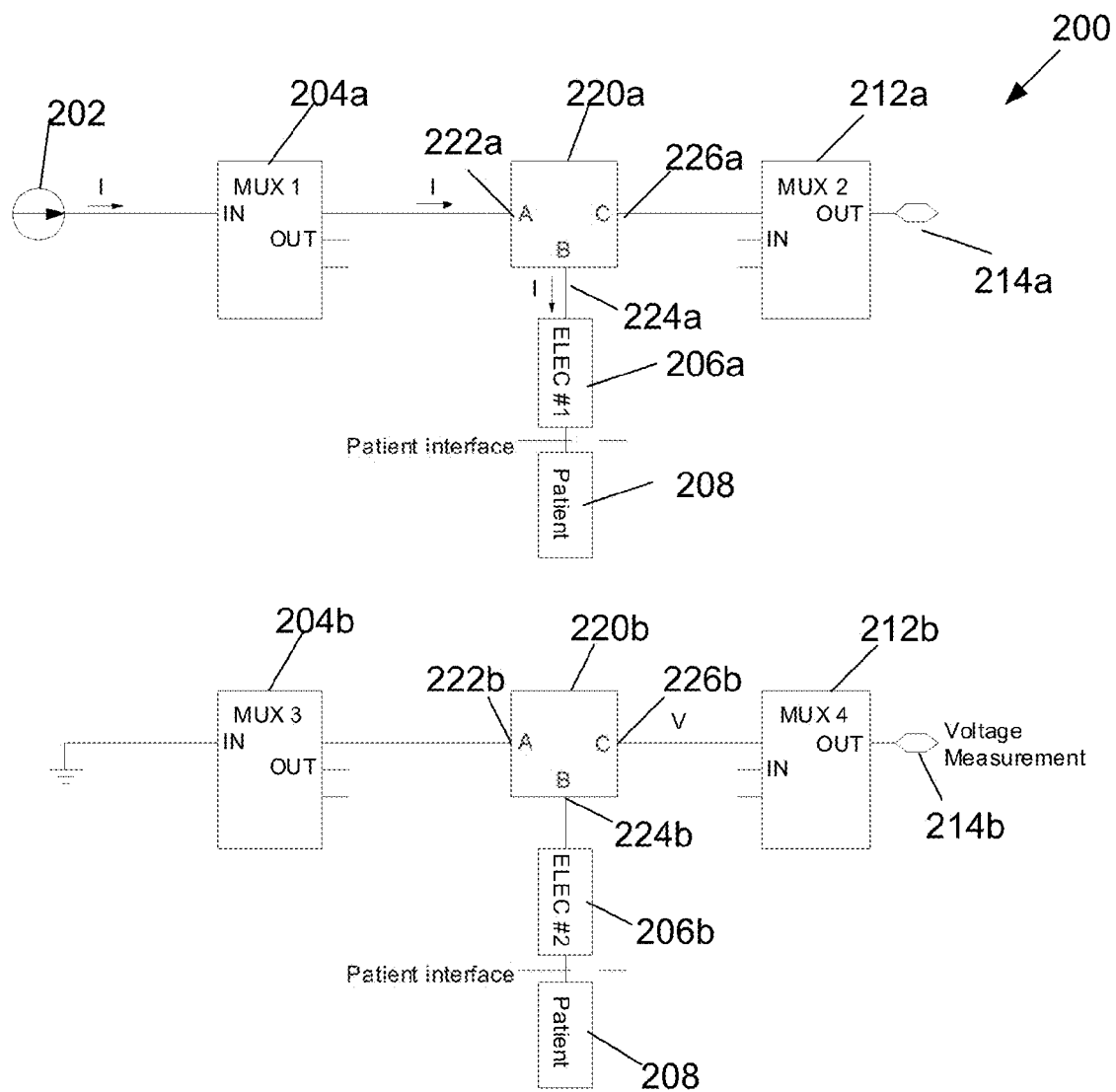
FIG. 3 is a schematic diagram of the current multiplexing system of FIG. 2 showing additional components.

Reference is now made to FIG. 3, which illustrates two current delivery circuits 220a and 220b of the current multiplexing system 200 of FIG. 2. As was mentioned above with reference to FIG. 2, in various embodiments, current multiplexing system 200 comprises a plurality of current delivery circuits 220 and a plurality of electrodes. FIG. 2 illustrates only a single current delivery circuit and a single electrode for reasons of clarity. However, as mentioned above, in various embodiments, current multiplexing system 200 comprises at least two current delivery circuits and at least two electrodes, where one electrode can be a current delivery electrode and the second electrode can be a current return electrode.

FIG. 3 illustrates two current delivery circuits and two electrodes. It should be understood however that a greater number could be used. Nonetheless, in some embodiments, two current delivery circuits and two electrodes are sufficient. For example, but not limited to, electrode 206a could be used as a current delivery electrode and electrode 206b could be used as a current return electrode. In such embodiments, one of electrodes 206a and 206b could be used as a positive voltage measurement electrode and the other could be used as a negative voltage measurement electrode. The voltage at each of nodes 214a and 214b, which are the outputs of multiplexers 212a and 212b respectively, could be measured to obtain a differential voltage measurement between electrodes 206a and 206b. This may be referred to as a two point measurement given that two electrodes are used (for both current injection/return and for voltage measurement) and therefore there are two points of contact between the current multiplexing system and the patient.

FIG. 3, shows the input of multiplexer 204b connected to ground. In various other embodiments used for a two point measurement, the input of multiplexer can be, for example but not limited to, connected to a second current source (not shown) that is complimentary to current source 202. More specifically, the second current source could have the second amplitude and opposite phase such that when current source 202 "pushes" current into patient 208 through electrode 206a, the second current source "pulls" current from the patient through electrode 206b. As will be apparent to those skilled in the art, this can provide a virtual ground in the patient.

In various other embodiments, a greater number of electrodes could be used for current injection/return and voltage measurement. For example, but not limited to, a four point measurement could be used. A four point measurement can use four electrodes, where one electrode is used as a current injection electrode, a second electrode could be used as a current return electrode, a third electrode could be used as a positive voltage measurement electrode, and a fourth electrode could be used as a negative voltage measurement electrode.

Referring back to FIG. 3, electrode 206a could be used as a current injection electrode and electrode 206b could be used as voltage measurement electrode. Thus, it will be appreciated that in this example, the current delivery circuit 220b is actually acting to deliver a sensed voltage signal. It will be appreciated from this that the circuit can be more generally referred to as a signal delivery circuit. In this example, the apparatus of FIG. 3 can be combined with a current return electrode and a second voltage measurement electrode so a four point measurement system would result, for example to allow tetrapolar impedance measurements to be performed.

In various embodiments, an AC current such as sinusoidal waveform with no DC offset can be used and therefore in such embodiments the application of the terms current injection and current return to an electrode is arbitrary. More specifically, in such an embodiment, a given electrode will be conducting current in one direction half of the time and conducting it in the other direction for the other half. For similar reasons; the application of the terms positive and negative voltage measurement to an electrode can also be arbitrary.

In addition, when a four point measurement is used, a more accurate voltage measurement may be obtained. Specifically, substantially no current will be moving through the voltage measurement electrodes and therefore the impedance of the electrodes and the interface between the electrode and patient will not significantly distort the voltage measurement.

Figure 4:
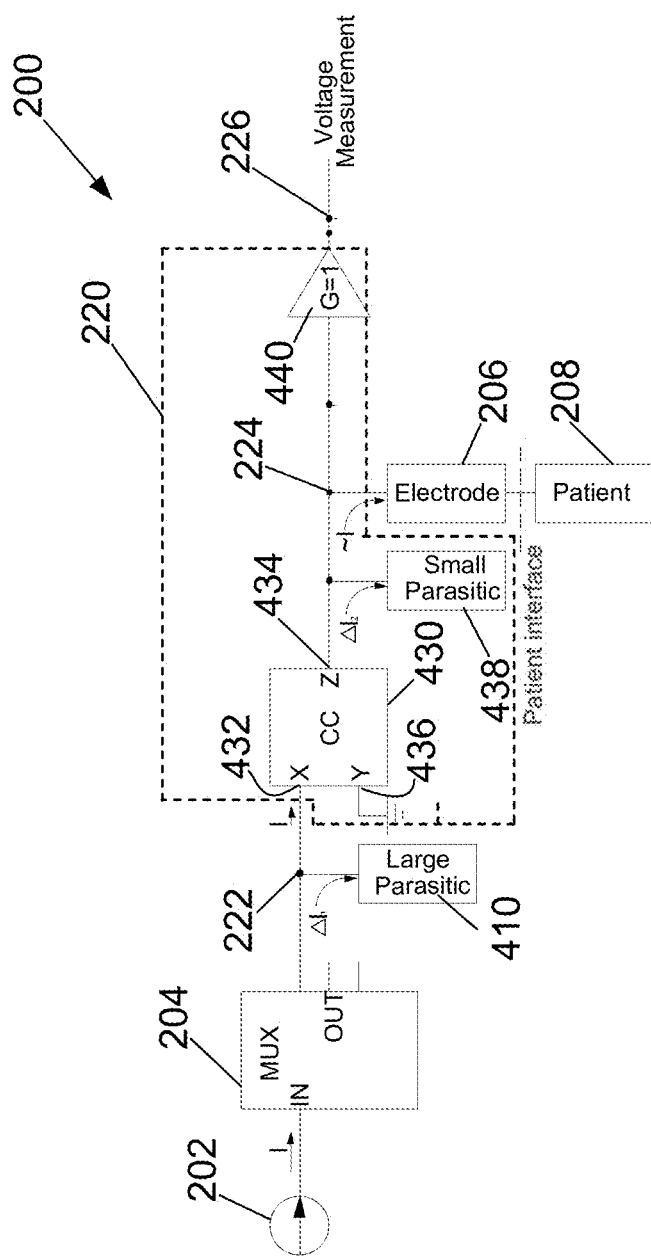
FIG. 4 is a schematic diagram of the current multiplexing system of FIG. 2 showing the current delivery circuit in greater detail.

Reference is now made to FIG. 4, which a block diagram illustrating a portion of the current multiplexing system 200 of FIG. 2 in greater detail. Multiplexer 204 causes a large parasitic impedance to appear at its outputs such as at node 222. Electrode 206 is coupled to the current delivery circuit at node 224. Node 226, which is the output of current delivery circuit 220 can be used to measure the voltage that appears at electrode 206. Optionally, node 226 can be connected to the input of a multiplexer, which may be useful when there are many electrodes 206 and current delivery circuits 220 being used.

In some embodiments, current delivery circuit 220 comprises a current buffer 430 and a voltage buffer 440. Current buffer 430 introduces parasitic impedance 438 to appear at node 224. In some embodiments, current buffer 430 can be a current conveyor as shown in FIG. 4. The input 432 of current buffer 430 is coupled to node 222. The output 434 of current buffer 430 is coupled to node 224. If a current conveyor is used as the current buffer then its other input 436 can be connected to ground.

In various embodiments according to applicants' teachings, current buffer 430 is designed so as to have a low input impedance at input 432. Consequently, the leakage current ($\Delta I_1$) lost to parasitic impedance 410 is minimal. In addition, current buffer 430 is designed so as to present only a small parasitic impedance to node 224. As a result most of the current that is outputted through output 434 passes through electrode 206 and only a minimal amount of leakage current ($\Delta I_2$) is lost to parasitic impedance 438. In addition, in various embodiments, current buffer 430 is designed to have a high output impedance, which maximizes the amount of current delivered to the patient electrode. The combination of the above features can be achieved for example by implementing current buffer 430 as a current conveyor. However, in some other embodiments other appropriate current buffers with similar, features can also be used.

In some embodiments, voltage buffer 440 can be selected to have a high input impedance so that the voltage at node 224 can be reproduced at node 226 without affecting the voltage at node 224. In various embodiments, this allows for standardized non-invasive voltage measurements to be made at node 226.

In various embodiments, current multiplexing system 200 can be used without a calibration step even when the loads are changed. For example, a calibration step is not required when a electrodes 206 is coupled to a new, patient. In addition, in various embodiments, current multiplexing system 200 can be used without modifying or otherwise manipulating the patient electrode interface.

In various embodiments, current delivery circuit 220 can be integrated on a single integrated circuit. In some embodiments, a plurality of current delivery circuit 220 can be integrated on a single integrated circuit and packaged in a single chip.

It should be understood that in various embodiments any appropriate scheme could be used to switch or multiplex various inputs to each current injection circuit 220. Regardless of the switching or multiplexing scheme utilized a resulting parasitic capacitance 410 will result. Current buffer 430 isolates the electrode patient interface from interfering effects caused by the switches and their parasitic elements. Similarly, voltage buffer 440 isolates electrode 206 (and thereby the patient electrode interface) from interfering effects that may otherwise be caused by components beyond the voltage buffer 440.

Accordingly, in one example, the apparatus can be used to supply a drive signal to an electrode attached to the biological subject, and sense a signal at the electrode. Whilst the above example has focussed on the delivery of a current and measurement of a voltage, this is not essential, and the drive signal could be a voltage signal, with a current signal being measured. Alternatively, the signal delivery circuit could be used to measure the drive signal applied to the subject, allowing this to be used for example in calculating impedance measurements or the like. This may be performed to ensure that the magnitude and phase of the drive signal which is used in impedance calculations is as accurate as possible.

Accordingly, in general terms, the apparatus includes a signal delivery circuit including first and second buffers. The first buffer includes a first buffer input for receiving a signal from a signal source and a first buffer output for supplying a drive signal to an electrode attached to the biological subject. Similarly, the second buffer includes a second buffer input coupled to the first buffer output and a second buffer output for providing a sensed signal indicative of a signal at the electrode, to a sensor.

In one example, the first buffer is a current buffer and the second buffer a voltage buffer, allowing a drive current to be applied to the subject, and to allow a voltage at the electrode to be sensed. However, in alternative examples, a voltage signal may be applied to the subject and a current flow through the subject measured.

The signal delivery circuit allows a drive signal to be applied to the subject via an electrode and then a signal measured at the electrode. In one example, the measured signal is indicative of a signal, such as a potential, across the biological subject, with a single electrode is used as both a drive a sense electrode. However, this is not essential, and in another example, first and second current delivery circuits can be coupled to drive and sense electrodes respectively.

Accordingly, in one example, the first signal delivery circuit can include a first buffer having a first buffer input for receiving a signal from the signal source and a first buffer output for supplying the drive signal to the drive electrode and a second buffer having a second buffer input coupled to the first buffer output and a second buffer output for providing a sensed signal indicative of the drive signal at the drive electrode. This allows the magnitude of the drive signal injected into the biological subject to be measured, allowing this value to be used in performing impedance determination or the like. In this example, if the drive signal is a current signal, the second buffer is typically an amplifier having inputs in parallel with a resistor positioned between the first buffer output and the electrode, thereby allowing the current injected into the subject to be measured.

In this example, the second signal delivery circuit can include a first buffer having a first buffer input coupled to ground and a first buffer output coupled to the sense electrode and a second buffer having a second buffer input coupled to the first buffer output and a second buffer output for providing a sensed signal indicative of a signal at the sense electrode.

Figure 5:
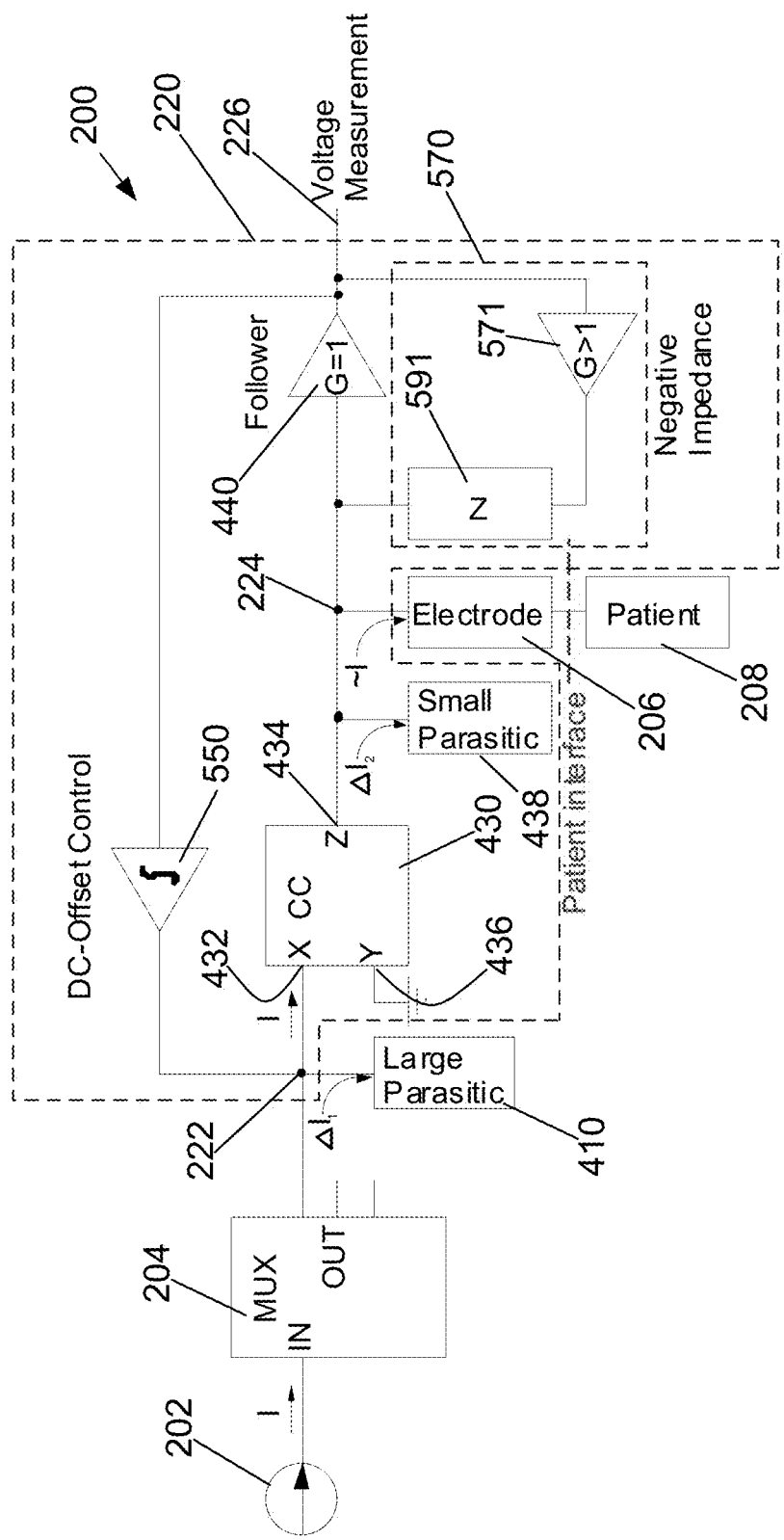
FIG. 5 is a schematic diagram of the current multiplexing system of FIG. 4 showing additional components.

Reference is now made to FIG. 5, which is a schematic diagram of the current multiplexing system of FIG. 4 showing additional components. In various embodiments, current delivery circuit 200 can also comprise a DC offset control circuit 550. In some embodiments, DC offset control circuit 550 is coupled in a feedback loop of the current buffer 430. More specifically, DC offset control circuit 550 is connected between node 226 and node 222. In various embodiments, DC offset control circuit 550 is used to control the DC offset or DC bias at node 224. However, DC offset control circuit 550 is coupled to node 222 so as not to disturb the electrode-patient interface which exists between electrode 206 and patient 208. This use of DC offset control circuit 550 can increase the accuracy of the measurements made using current multiplexing system 200.

In various embodiments, current delivery circuit 200 can also comprise a negative impedance circuit 570. Negative impedance circuit 570 can be used to compensate for parasitic impedance 438 introduced by current buffer 430 or other circuit elements at, for example, node 224. Negative impedance circuit 570 comprises an amplifier 571 and a compensation impedance 591. In various embodiments, voltage amplifier 571 has a gain value greater than 1. Negative impedance circuit 570 can be used to provide a current to node 224 that is substantially equal to the leakage current ($\Delta I_2$) that is lost from node 224 through parasitic impedance 438. The operation of negative impedance circuit 570 will be discussed in greater detail below.

It should be understood that the use of DC offset control circuit 550 is optional. It should also be understood that the use of negative impedance circuit 570 is optional. It should be further understood that DC offset control circuit 550 and negative impedance circuit 570 can be used independently of each other. Therefore, various embodiments can utilize either of one DC offset control circuit 550 and negative impedance circuit 570, both DC offset control circuit 550 and negative impedance circuit 570, or neither.

It should further be understood that in various embodiments, DC offset control circuit 550 and negative impedance circuit 570 can be integrated as part of current delivery circuit 220. In various other embodiments, either or both of DC offset control circuit 550 and negative impedance circuit 570 can be separate circuits. For example, but not limited to, in some embodiments, multiplexers could be used to couple either of these circuit to a particular current delivery circuit.

Figure 6:
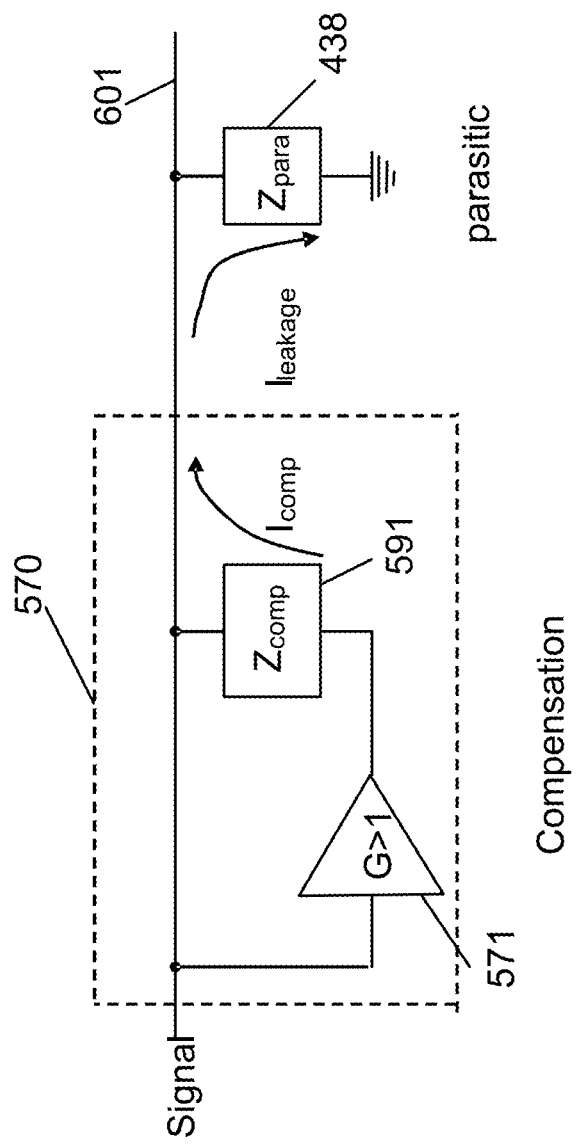
FIG. 6 is a schematic diagram of the negative impedance of FIG. 5.

Reference is now made to FIG. 6, which is a schematic diagram of a circuit 600 comprising a transmission channel 601, a parasitic impedance 438 shunting the transmission line, and a negative impedance circuit 570. Transmission channel 601 can, for example, correspond to node 224. Negative impedance circuit 570 comprises a voltage amplifier 571 and compensation impedance 591. The input of the amplifier 571 is coupled to the signal-transmission channel 601 and the output is coupled to one terminal of the compensation impedance 591. The other terminal of the compensation impedance is coupled to the signal-transmission channel.

Signal-transmission channel 601 may be used to transmit a current to a load (not shown), which may be any suitable circuit or circuit component, such as for example an electrode. The presence of a signal on signal-transmission channel 601 causes a voltage to appear across parasitic impedance 438. This causes a leakage current $I_{leakage}$ to flow through the parasitic impedance 438. The magnitude of the current flowing through parasitic impedance 438 depends on the value of the impedance as well as the magnitude of the voltage appearing across its terminals.

Amplifier 571 amplifies the signal appearing on the signal-transmission channel 601. In various embodiments, amplifier 571 has a gain that is greater than 1. This causes a voltage to appear across compensation impedance 591 and a current $I_{comp}$ to flow through compensation impedance 591.

In various embodiments, the gain of amplifier 571 and the value of the compensation impedance is selected such that the current that flows through parasitic impedance 438 is compensated for by the current that flows through compensation impedance 591. Specifically, given a signal voltage of $V_{signal}$, a parasitic impedance of $Z_{para}$, the leakage current can be said to be:

$$I_{leakage} = V_{signal} \times \left(\frac{1}{Z_{para}}\right) \quad \text{Equation (1)}$$

Similarly, given a compensation impedance of $Z_{comp}$ and an amplifier gain of G, the compensation current flowing through the compensation current may be said to be:

$$I_{comp} = V_{signal} \times (G-1) \times \left(\frac{1}{Z_{comp}}\right) \quad \text{Equation (2)}$$

Equating equation (1) and equation (2) yields the following:

$$I_{comp} = I_{leakage} \quad \text{Equation (3)}$$
$$\left(\frac{G-1}{Z_{comp}}\right) = \frac{1}{Z_{para}}$$

Thus, by selecting G and $Z_{comp}$ to satisfy equation (3) the compensation current will exactly match the leakage current. The compensation impedance 591 effectively serves as a negative impedance that cancels the effect of the parasitic impedance 438.

In various embodiments, the value of the parasitic impedance may not be known and therefore it may not be possible to select a gain for the amplifier by simply using equation (3) above. In such embodiments, the value of the gain can be estimated by using circuit 600 of FIG. 6. Specifically, circuit 600 is implemented by selecting a compensation impedance and range of values of gain. The circuit is operated at the various values of gain and the output is monitored. For those values of gain that exceed the required value the output would oscillate. Thus, the correct value of the gain lies in a range of values that is bounded by (1) the lowest known value of the gain at which the output oscillates and (2) the highest known value of the gain at which the output does not oscillate. This process may be continued in an iterative manner until a suitable value of gain is selected. Once an appropriate value of gain is determined, the parasitic impedance may be estimated by using equation (3) given above.

In various embodiments, the parasitic impedance may be comprised of both capacitive and resistive elements. However, in some embodiments the effect of the capacitive loading can be significantly greater than the effect of the resistive loading. In such cases, various embodiments of applicants' teachings may be used to address the capacitive loading and not the resistive loading. Alternatively, applicants' teachings may be used to partially compensate for any portion of the parasitic impedance. Thus, in various embodiments, circuits according to applicants' teachings may be used to reduce and partially compensate for any leakage currents that may flow through any parasitic impedances coupled to a signal-transmission channel, but not necessarily to completely compensate for all the current that is lost due to leakage currents.

Alternatively, the parasitic impedance may be measured or estimated according to known techniques. The value of the parasitic impendence obtained from this may then be used to select initial values for the compensation impedance and the range of values of gain. The gain can then be fine tuned according to the above-described method.

Figure 7:
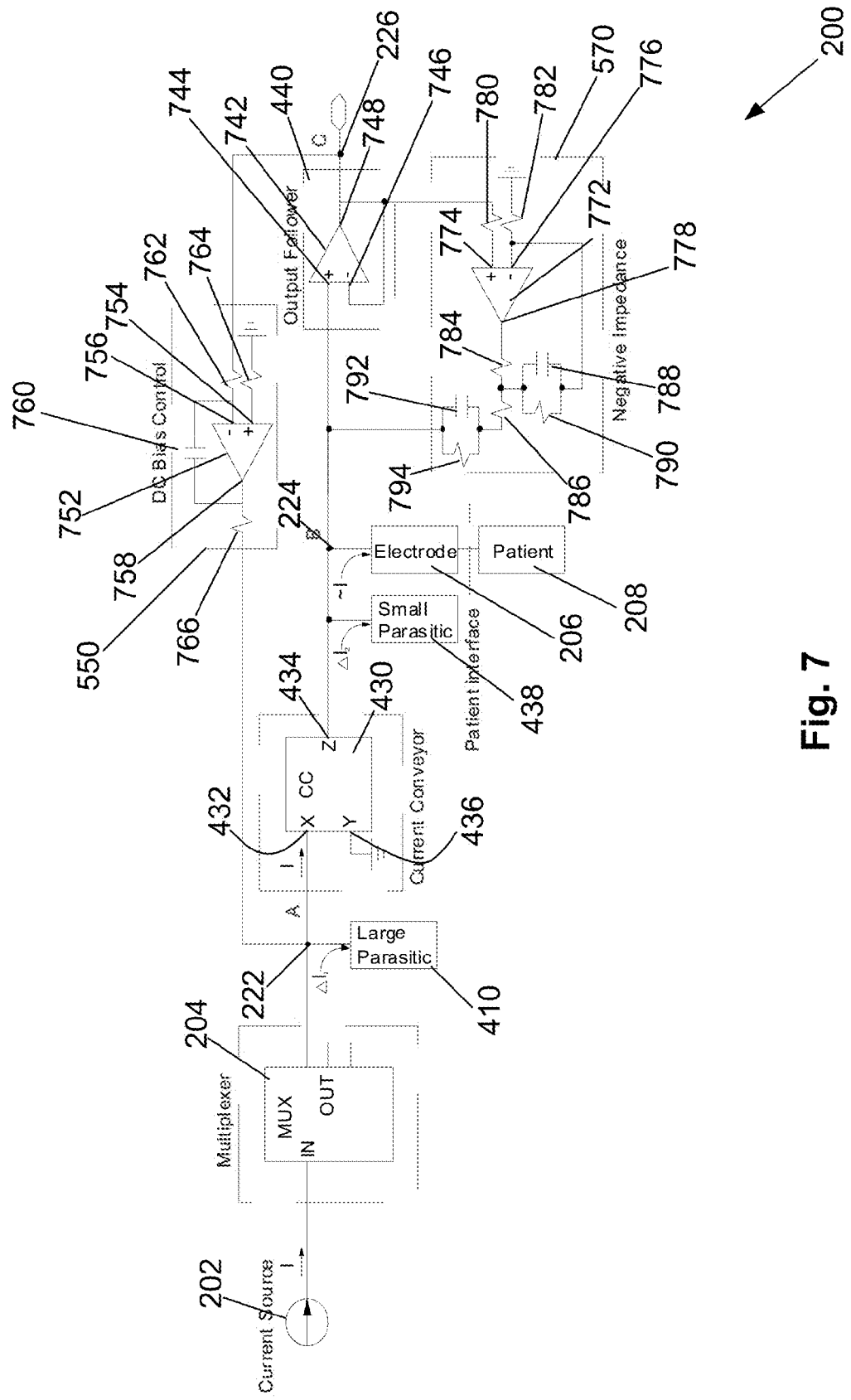
FIG. 7 is a schematic diagram of the current multiplexing system of FIG. 5 showing the DC bias control and negative impedance in greater detail.

Reference is now made to FIG. 7, which is a schematic diagram of the current multiplexing system of FIG. 5, showing the DC bias control and negative impedance in greater detail. In various embodiments, voltage buffer 440 comprises an operational amplifier 742 connected as an output follower. More specifically, non-inverting input 744 is coupled to node 224; while, inverting node 746 and output 748 are coupled to node 226.

In various embodiments, negative impedance circuit 570 comprises an operational amplifier 772 with non-inverting input 774, inverting input 776 and output 778. Resistor 780 is connected between node 226 and non-inverting input 774. Resistor 782 is coupled between inverting input 776 and ground. One terminal of resistor 784 is coupled to output 778 and the other terminal of resistor 784 is coupled to resistor 786. Capacitor 788 and resistor 790 are each coupled between non-inverting input 776 and the common terminal of resistors 784 and 786. Capacitor 792 and resistor 794 are coupled between node 224 and resistor 786. Negative impedance circuit will be discussed in greater detail below.

In some embodiments DC-offset control circuit 550 comprises an operational amplifier 752 connected as an integrator. Specifically, operational amplifier 752 has non-inverting input 754, inverting input 756 and output 758. Capacitor 760 is connected between inverting input 756 and output 758. Resistor 762 is connected between inverting input 756 and node 226. Resistor 764 is connected between the non-inverting input 754 and ground. Resistor 766 is connected between output 758 and node 222.

Figure 8:
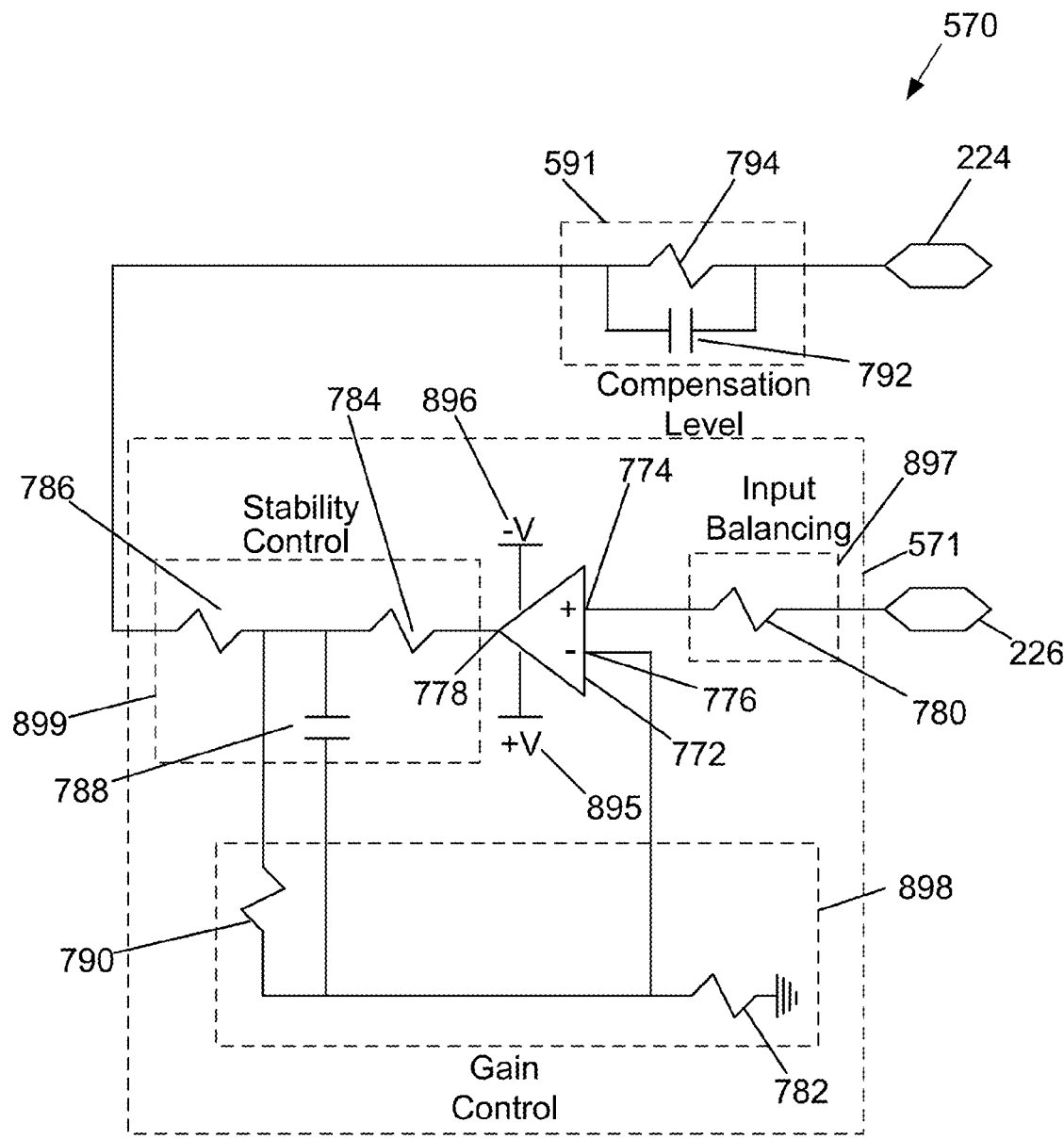
FIG. 8 is a schematic diagram of the negative impedance of FIG. 7.

Reference is now made to FIG. 8, which is a schematic diagram of negative impedance circuit 570 of FIG. 7. For greater clarity FIG. 8 illustrates negative impedance circuit 570 apart from the rest of current multiplexing system 200.

Negative impedance circuit 570 comprises an amplifier portion 571 having an operational amplifier 772 with a non-inverting input 774, an inverting input 776, an output node 778. Operational amplifier 772 also comprises power rails 895 and 896.

Referring again to the amplifier portion 571, amplifier portion 571 further comprises an input balancing portion 897, a gain control portion 898, and a stability control portion 899. Input balancing portion 897 comprises resistor 780, which is connected between node 226 and non-inverting input 774. Gain control portion 898 comprises resistor 782 and resistor 790. By adjusting the values of resistors 782 and 790, one is able to adjust the gain G of the overall amplifier portion 771. In various embodiments, the values of resistors 782 and 790 may be set to a value that is greater than 1. Stability control portion 899 comprises capacitor 788, resistor 784, and resistor 794. By adjusting the values of capacitor 788, resistor 784, and resistor 794 one is able to alter the stability of the overall amplifier circuit.

In various embodiments, negative impedance circuit 570 also comprises compensation impedance 591. Compensation impedance 591 is in turn comprised of resistor 794 and capacitor 792, both of which are connected between node 224 and stability control portion 899. Compensation impedance 591 is used to compensate for parasitic impedance 438 of FIG. 7. By adjusting gain control portion 898 and compensation impedance 591, one may adjust the compensation current that is provided to the signal-transmission channel, and thereby match the compensation current magnitude to the magnitude of the leakage current. This may be done according to equation (3) given above.

Whilst the above examples have focussed on the use of a current source, this is not essential, and alternatively the system may use a voltage source, with the generated voltage being used to inject a drive signal in the form of a current into a subject, with the magnitude of the drive signal being measured using a sensor at node 214.

From this, it will be appreciated that the current delivery circuit 220 can be referred to more generally as a signal delivery circuit. Similarly, the current and voltage buffers can be first and second buffers for supplying a drive signal to an electrode attached to the biological subject, and for providing a signal indicative of a signal at the electrode.

As mentioned above, the signal delivery circuit can be used in a variety of different systems. In one example, the signal delivery circuit can be incorporated into apparatus suitable for performing an analysis of a subject's bioelectric impedance, an example of which will now be described with reference to FIG. 9.

As shown the apparatus includes a measuring device 900 including a processing system 902, connected to one or more signal generators 917A, 917B, via respective first leads 923A, 923B, and to one or more sensors 918A, 918B, via respective second leads 925A, 925B.

In use, the signal generators 917A, 917B are coupled to two first electrodes 913A, 913B, via drive signal delivery circuits 919A, 919B, which therefore act as drive electrodes to allow signals to be applied to the subject S, whilst the one or more sensors 918A, 918B are coupled to the second electrodes 915A, 915B, via sensed signal delivery circuits 920A, 920B, which act as sense electrodes, allowing signals across the subject S to be sensed. It will be appreciated that the drive and sensed signal delivery circuits are similar to the delivery circuits described above in FIGS. 1 to 8.

In one example, a single signal generator 917 may be provided, coupled to the drive signal delivery circuits 919A, 919B and hence the drive electrodes 913A, 913B, via multiplexers 204a from the example of FIG. 3. Similarly a single sensor 918 can be coupled to the sensed signal delivery circuits 920A, 920B and hence the sense electrodes 915A, 915B, via multiplexers, such as the multiplexers 212b from the example of FIG. 3.

However, this is not essential, and alternatively first and second signal generators 917A, 917B and sensors 918A, 918B can be used, each being coupled to the corresponding electrodes 913A, 913B, 914A, 914B via respective signal delivery circuits. This is particularly useful if the arrangement is used to perform balancing, as will be described in more detail below.

Accordingly, this provides apparatus for use in performing impedance measurements on a subject which includes a signal source for applying a signal to a subject, a sensor for sensing signals from the subject, a processing system for controlling the signal source and receiving signals from the sensor and at least one signal delivery circuit, including a first buffer having: a first buffer input for receiving a signal from a signal source and a first buffer output for supplying a drive signal to an electrode attached to the biological subject and a second buffer having a second buffer input coupled to the first buffer output and a second buffer output for providing a sensed signal indicative of a signal at the electrode, to a sensor.

In one example, at least one signal delivery circuit is used for supplying a current to a drive electrode attached to the biological subject and at least one signal delivery circuit for providing a voltage signal indicative of a voltage at a sense electrode.

Additional features of the impedance measurement apparatus will now be described.

The signal generators 917A, 917B and the sensors 918A, 918B may be provided at any position between the processing system 902 and the electrodes 913A, 913B, 915A, 915B, and may be integrated into the measuring device 900. However, in one example, the signal generators 917A, 917B and the sensors 918A, 918B are integrated into an electrode system, or another unit provided near the subject S, with the leads 923A, 923B, 925A, 925B connecting the signal generators 917A, 917B and the sensors 918A, 918B to the processing system 902.

It will be appreciated that the above described system is a two channel device, used to perform a classical four-terminal impedance measurement, with, each channel being designated by the suffixes A, B respectively. The use of a two channel device is for the purpose of example only, as will be described in more detail below.

An optional external interface 903 can be used to couple the measuring device 900, via wired, wireless or network connections, to one or more peripheral devices 904, such as an external database or computer system, barcode scanner, or the like. The processing system 902 will also typically include an I/O device 905, which may be of any suitable form such as a touch screen, a keypad and display, or the like.

In use, the processing system 902 is adapted to generate control signals, which cause the signal generators 917A, 917B to generate one or more alternating signals, such as voltage or current signals of an appropriate waveform, which can be applied to a subject S, via the first electrodes 913A, 913B. The sensors 918A, 918B then determine the voltage across or current through the subject S, using the second electrodes 915A, 915B and transfer appropriate signals to the processing system 902, for analysis. In the event that the apparatus includes multiplexers for coupling signal generators or sensors to respective signal delivery circuits, the processing system would also typically act to control the multiplexers allowing signals to be delivered to and measured across the subject as required.

Accordingly, it will be appreciated that the processing system 902 may be any form of processing system which is suitable for generating appropriate control signals and at least partially interpreting the measured signals to thereby determine the subject's bioelectrical impedance, and optionally determine other information such as relative fluid levels, or the presence, absence or degree of conditions, such as oedema, lymphoedema, measures of body composition, cardiac function, or the like.

The processing system 902 may therefore be a suitably programmed computer system, such as a laptop, desktop, PDA, smart phone or the like. Alternatively the processing system 902 may be formed from specialised hardware, such as an FPGA (field programmable gate array), or a combination of a programmed computer system and specialised hardware, or the like, as will be described in more detail below.

In use, the first electrodes 913A, 913B are positioned on the subject to allow one or more signals to be injected into the subject S. The location of the first electrodes will depend on the segment of the subject S under study. Thus, for example, the first electrodes 913A, 913B can be placed on the thoracic and neck region of the subject S to allow the impedance of the chest cavity to be determined for use in cardiac function analysis. Alternatively, positioning electrodes on the wrist and ankles of a subject allows the impedance of limbs and/or the entire body to be determined, for use in oedema analysis, or the like.

Once the electrodes are positioned, one or more alternating signals are applied to the subject S, via the first leads 923A, 923B and the first electrodes 913A, 913B. The nature of the alternating signal will vary depending on the nature of the measuring device and the subsequent analysis being performed.

For example, the system can use Bioimpedance Analysis (BIA) in which a single low frequency signal (typically <50 kHz) is injected into the subject S, with the measured impedance being used directly in the assessment of relative intracellular and extracellular fluid levels. In contrast Bioimpedance Spectroscopy (BIS) devices utilise frequencies ranging from very low frequencies (4 kHz) to higher frequencies (1000 kHz), and can use as many as 256 or more different frequencies within this range, to allow multiple impedance measurements to be made within this range.

Thus, the measuring device 900 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with each of the signal generators 917A, 917B being independently controllable, to allow the signal voltage across the subject to be varied.

A voltage difference and/or current is measured between the second electrodes 915A, 915B. In one example, the voltage is measured differentially, meaning that each sensor 918A, 918B is used to measure the voltage at each second electrode 915A, 915B and therefore need only measure half of the voltage as compared to a single ended system.

The acquired signal and the measured signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce amplitude and phase signals at each frequency.

As part of the above described process, the distance between the second electrodes 915A, 915B may be measured and recorded. Similarly, other parameters relating to the subject may be recorded, such as the height, weight, age, sex, health status, any interventions and the date and time on which they occurred. Other information, such as current medication, may also be recorded. This can then be used in performing further analysis of the impedance measurements, so as to allow determination of the presence, absence or degree of oedema, to assess body composition, or the like.

The accuracy of the measurement of impedance can be subject to a number of external factors. These can include, for example, the effect of capacitive coupling between the subject and the surrounding environment, the leads and the subject, the electrodes, or the like, which will vary based on factors such as lead construction, lead configuration, subject position, or the like. Additionally, there are typically variations in the impedance of the electrical connection between the electrode surface and the skin (known as the "electrode impedance"), which can depend on factors such as skin moisture levels, melatonin levels, or the like. A further source of error is the presence of inductive coupling between different electrical conductors within the leads, or between the leads themselves.

Such external factors can lead to inaccuracies in the measurement process and subsequent analysis and accordingly, it is desirable to be able to reduce the impact of external factors on the measurement process.

One form of inaccuracy that can arise is caused by the voltages across the subject being unsymmetrical, a situation referred to as an "imbalance". Such a situation results in a significant signal voltage at the subject's body centre, which in turn results in stray currents arising from parasitic capacitances between the subject's torso and the support surface on which the subject is provided.

The presence of an imbalance, where the voltage across the subject is not symmetrical with respect to the effective centre of the subject, leads to a "common mode" signal, which is effectively a measure of the signal at the subject S that is unrelated to the subject's impedance.

To help reduce this effect, it is therefore desirable for signals to be applied to the subject S that they result in a symmetrical voltage about the subject's body centre. As a result, a reference voltage within the subject S, which is equal to a reference voltage of the measurement apparatus, will be close to the effective body centre of the subject, as considered relative to the electrode placement. As the measuring device reference voltage is typically ground, this results in the body centre of the subject S being as close to ground as possible, which minimises the overall signal magnitude across the subject's torso, thereby minimising stray currents.

In one example, a symmetrical voltage about the sensing electrodes can be achieved by using a symmetrical voltage source, such as a differential bidirectional voltage drive scheme, which applies a symmetrical voltage to each of the drive electrodes 913A, 913B. However, this is not always effective if the contact impedances for the two drive electrodes 913A, 913B are unmatched, or if the impedance of the subject S varies along the length of the subject S, which is typical in a practical environment.

In one example, the apparatus overcomes this by adjusting the differential voltage drive signals applied to each of the drive electrodes 913A, 913B, to compensate for the different electrode impedances, and thereby restore the desired symmetry of the voltages across the subject S. This process is referred to herein as balancing and in one example, helps reduce the magnitude of the common mode signal, and hence reduce current losses caused by parasitic capacitances associated with the subject.

The degree of imbalance, and hence the amount of balancing required, can be determined by monitoring the signals at the sense electrodes 915A, 915B, and then using these signals to control the signal applied to the subject via the drive electrodes 913A, 913B. In particular, the degree of imbalance can be calculated by determining an additive voltage from the voltages detected at the sense electrodes 915A, 915B.

In one example process, the voltages sensed at each of the sense electrodes 915A, 915B are used to calculate a first voltage, which is achieved by combining or adding the measured voltages. Thus, the first voltage can be an additive voltage (commonly referred to as a common mode voltage or signal) which can be determined using a differential amplifier.

In this regard, a differential amplifier is typically used to combine two sensed voltage signals $V_a$, $V_b$, to determine a second voltage, which in one example is a voltage differential $V_a-V_b$ across the points of interest on the subject S. The voltage differential is used in conjunction with a measurement of the current flow through the subject to derive impedance values. However, differential amplifiers typically also provide a "common mode" signal $(V_a+V_b)/2$, which is a measure of the common mode signal.

Whilst differential amplifiers include a common mode rejection capability, this is generally of only finite effect and typically reduces in effectiveness at higher frequencies, so a large common mode signal will produce an error signal superimposed on the differential signal.

The error caused by common mode signals can be minimised by calibration of each sensing channel. In the ideal case where both inputs of a differential amplifier are perfectly matched in gain and phase characteristics and behave linearly with signal amplitude, the common mode error will be zero. In one example, the two sensing channels of the differential amplifier are digitised before differential processing. It is therefore straightforward to apply calibration factors independently to each channel to allow the characteristics to be matched to a high degree of accuracy, thereby achieving a low common mode error.

Accordingly, by determining the common mode signal, the applied voltage signals can be adjusted, for example by adjusting the relative magnitude and/or phase of the applied signals, to thereby minimise the common mode signal and substantially eliminate any imbalance.

Figure 9:
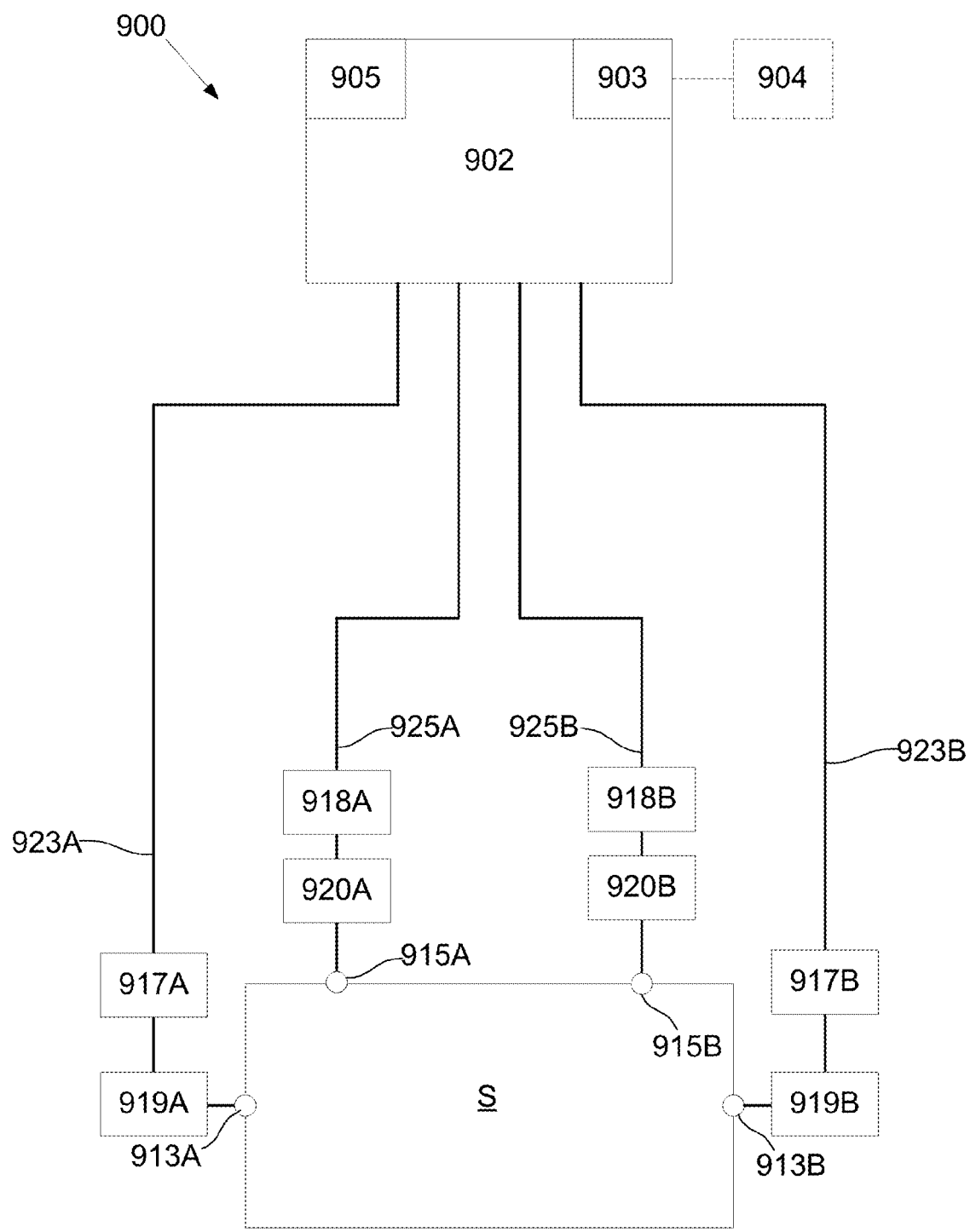
FIG. 9 is a schematic diagram of an example of an impedance measuring device; and, FIG. 10 is a flowchart of an example of a process for performing impedance measuring.
Figure 10:
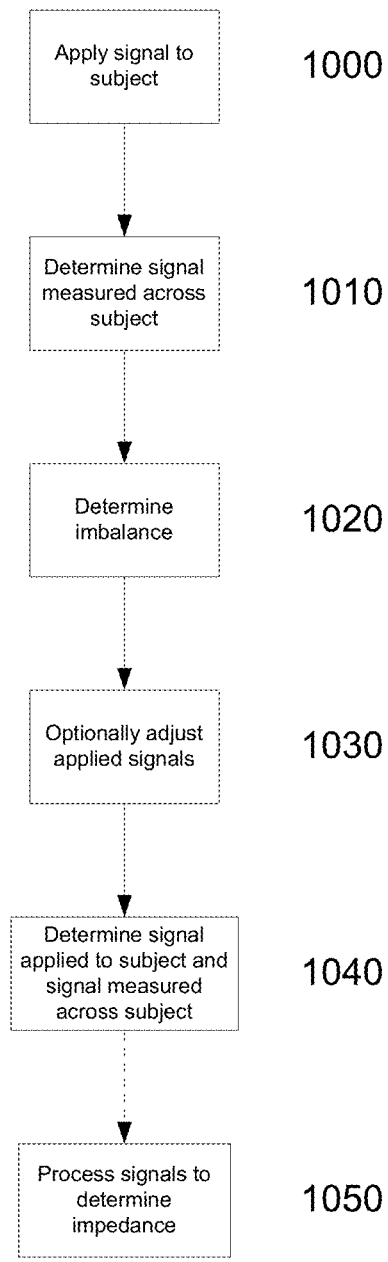

An example of the operation of the apparatus of FIG. 9 to perform this will now be described with reference to FIG. 10.

At step 1000, a first signal is applied to the subject S, with a second signal measured across the subject S being determined at step 1010. This will typically be achieved using the techniques outlined above. Accordingly, the processing system 902 will cause the signal generators 917A, 917B to generate the first signal, which is typically applied to the subject S via the first electrodes 913A, 913B. Similarly the second signal will be sensed by the sensors 918A, 918B, via the second electrodes 915A, 915B, with an indication of the second signal being provided to the processing system 902.

At step 1020, an imbalance is determined by the processing system 902 using the second signal sensed at the second electrodes 915A, 915B, which in one example represents a common mode signal.

At step 1030, the measuring device optionally adjusts the first signal applied to the subject S, so as to reduce the imbalance and hence the magnitude of the common mode signal. Thus, the magnitude of the signal applied at either one of the first electrodes 913A, 913B can be adjusted, for example by increasing or decreasing the relative signal magnitudes and/or altering the relative signal phases, so as to balance the signal within the subject and centralise the position of the reference voltage within the subject relative to the electrode positioning.

At step 1040, the measuring device can then determine the signal applied to the subject and the voltages measured at the electrodes 913A, 913B, thereby allowing an impedance to be determined at step 1050.

As the position of the reference voltage within the subject S is impedance dependent, the imbalance will typically vary depending on the frequency of the applied signal. Accordingly, in one example, it is typical to determine the imbalance and adjust the applied signal at each applied frequency. However, this may depend on the preferred implementation.

An example of balancing procedure and operation of an impedance measuring device is described in more detail in the copending patent application number WO2009/059351, and this will not therefore be described in any further detail herein.

In various examples, applicants' teachings relate to a current delivery circuit. In various examples, the current delivery circuit comprises an input, a current output and a voltage output. In some examples, the current delivery circuit accepts a current at its input and produces a proportional output current at the current output. In various examples, current delivery circuit produces an output voltage signal at the voltage output that is proportional to an input voltage signal appearing at the current delivery circuit current output.

In various examples according to applicants' teachings, the current delivery circuit comprises a current buffer and a voltage buffer. The current buffer and voltage buffer each have an input and an output. The current delivery circuit input is coupled to the current buffer input. The current buffer output is coupled to the current delivery circuit current output. The voltage buffer input is coupled to the current delivery circuit current output. The voltage buffer output is coupled to the current delivery circuit voltage output.

In some examples, the output current is substantially equal to the input current. In various examples, the output voltage signal is substantially equal to the input voltage signal.

In some examples, the current buffer is a current conveyor. In various examples, the voltage buffer is a voltage follower.

In various examples, the current delivery circuit further comprises a parasitic impedance coupled to the current buffer output. In some examples, the current delivery circuit further comprises a negative impedance coupled between, the voltage buffer output and the current buffer output for compensating for the parasitic impedance. In some examples, the negative impedance comprises: a compensation impedance having a compensation impedance value, a first terminal and a second terminal, the first terminal coupled to the voltage buffer input; a compensation amplifier having a compensation amplifier input, a compensation amplifier output and a gain, the compensation amplifier input coupled to the voltage buffer output, the compensation amplifier output coupled to the second terminal of the compensation impedance to provide a compensation current to flow through the impedance, and the gain and the compensation impedance values are selected based on the parasitic impedance value so that the compensation current has a magnitude substantially equal to the leakage current magnitude.

In various examples, current delivery circuit further comprises a DC offset control circuit coupled between the voltage buffer output and the current buffer input. In some examples according to applicants' teachings, the DC offset control comprises an integrator coupled between the voltage buffer output and the current buffer input.

In various examples, applicants' teachings relate to a current multiplexing circuit comprising one or more current multiplexers, each having an input and a plurality of outputs, and one or more current delivery circuits. In various examples, the outputs of the one or more current multiplexers are coupled to the input of each of the one or more current delivery circuits. In some examples, the current multiplexing circuit further comprises one or more voltage multiplexers. The voltage output of each of the one or more current delivery circuits is coupled to an input of the one or more voltage multiplexers.

In various examples, the circuit further comprises one or more current sources. In various examples, each current source is coupled to the input of the one or more current multiplexers.

In various examples, applicants' teachings relate to a current multiplexing system. In various examples, current multiplexing system comprises a first current delivery circuit and a second current delivery circuit. Current multiplexing system further comprises a first electrode coupled to the first current delivery circuit current output and a second electrode coupled to the second current delivery circuit current output.

In various examples, the voltage output of the first current delivery circuit is coupled to an input of a first voltage multiplexer and the voltage output of the second current delivery circuit is coupled to an input of a second voltage multiplexer. In various examples, the outputs of the first and second voltage multiplexers are adapted to provide first and second voltage measurement signals for allowing a differential voltage measurement.

In some examples, a first current source is coupled to the input of the first current delivery circuit. In some examples, the first current source is controllable to provide a constant alternating current. In some examples, the constant alternating current has a constant amplitude and constant phase. In various examples, the amplitude and phase are controllably variable.

In some examples, the input of the second current delivery circuit is coupled to ground. In various other examples, the input of the second current delivery circuit is coupled to a second current source. In various examples the second current source is complimentary to the first current source. As used herein, the term complimentary current source refers to a current source providing a current of equal magnitude with a 180° phase shift.

In some examples, the current multiplexing system further comprises one or more current multiplexers. Each current multiplexer has a first output coupled to the first current delivery circuit and a second output coupled to the second current delivery circuit. In some examples, the input of at least one of the current multiplexers is coupled to a first current source. In some examples, the input of at least one of the current multiplexers is coupled to a second current source. In some examples, the input of at least one of the current multiplexers is coupled to ground.

In some examples, the current multiplexing system further comprises a third and fourth current delivery circuit as well as a third and fourth electrode. The third electrode is coupled to the third current delivery circuit current output. The fourth electrode is coupled to the fourth current delivery circuit current output.

In some examples, the third current delivery circuit voltage output is coupled a first voltage multiplexer and the fourth current delivery circuit voltage output is coupled a second voltage multiplexer. In various examples, the outputs of the first and second voltage multiplexers are adapted to provide first and second voltage measurement signals for allowing a differential voltage measurement.

In some examples, the third and forth current delivery circuit inputs are coupled to ground.

In some examples of applicants' teachings, current multiplexing system comprises a current source, a current multiplexer, a current delivery circuit, an electrode, and an voltage multiplexer. The current source is coupled to an input of the current multiplexer. An output of the current multiplexer is coupled to the input of the current delivery circuits. A current output of the current delivery circuit is coupled to the electrode. A voltage output of the current delivery circuit is coupled to an input of the voltage multiplexer. In various examples the current multiplexing system further comprises an electrode coupled to the current output of the current delivery circuit.

Persons skilled in the art will appreciate that numerous variations and modifications will become apparent. All such variations and modifications which become apparent to persons skilled in the art, should be considered to fall within the spirit and scope that the invention broadly appearing before described.

Features from different examples above may be used interchangeably or in conjunction, where appropriate. Thus, for example, a range of different techniques are described for minimising errors and these can be used independently of each other, or in conjunction, depending on the particular implementation.

Furthermore, whilst the above examples have focussed on a biological subject such as a human, it will be appreciated that the measuring device and techniques described above can be used with any animal, including but not limited to, primates, livestock, performance animals, such as race horses, or the like.

The above described processes can be used for diagnosing the presence, absence or degree of a range of conditions and illnesses, including, but not limited to oedema, lymphoedema, body composition, or the like.

The claims defining the invention are as follows:

1. Apparatus for electrically connecting measurement apparatus to a biological subject, the apparatus including a signal delivery circuit including:
   a current buffer having:
      a current buffer input for receiving a signal from a signal source; and,
      a current buffer output for supplying a current to an electrode attached to the biological subject;
   a voltage buffer having:
      a voltage buffer input coupled to the current buffer output; and,
      a voltage buffer output for providing a voltage signal indicative of a voltage at the electrode, to a sensor; and
   a DC offset control circuit coupled between the voltage buffer output and the current buffer input.

2. Apparatus according to claim 1, wherein the current buffer is a current conveyor.

3. Apparatus according to claim 1, wherein the voltage buffer is an amplifier connected as an output follower.

4. Apparatus according to claim 1, wherein the DC offset control circuit includes an integrator coupled between the voltage buffer output and the current buffer input.

5. Apparatus according to claim 1, wherein the DC offset control circuit is used to control a DC offset at the electrode.

6. Apparatus according to claim 1, wherein the signal delivery circuit includes a negative impedance circuit coupled between the voltage buffer output and the current buffer output.

7. Apparatus according to claim 6, wherein the negative impedance circuit includes a negative impedance circuit amplifier and a compensation impedance.

8. Apparatus according to claim 7, wherein at least one of a gain of the negative impedance circuit amplifier and a value of the compensation impedance is selected to compensate for parasitic impedance losses.

9. Apparatus according to claim 6, wherein the negative impedance circuit includes:
   a compensation impedance having a compensation impedance value, a first terminal and a second terminal, the first terminal coupled to the current buffer output; and,
   a compensation amplifier having a compensation amplifier input, a compensation amplifier output and a gain, the compensation amplifier input coupled to the voltage buffer output, the compensation amplifier output coupled to the second terminal of the compensation impedance to provide a compensation current to flow through the impedance, and the gain and the compensation impedance values are selected based on a parasitic impedance value so that the compensation current has a magnitude substantially equal to a leakage current magnitude.

10. Apparatus according to claim 1, wherein the apparatus includes:
    a plurality of signal delivery circuits, each signal delivery circuit being for supplying a current to a respective electrode attached to the biological subject;
    at least one signal source; and,
    at least one first multiplexer for selectively connecting the signal source to one of the plurality of signal delivery circuits to thereby apply a current to the biological circuit via the respective electrode.

11. Apparatus according claim 1, wherein the apparatus includes:
    a plurality of signal delivery circuits, each signal delivery circuit being for providing a voltage signal indicative of a voltage at the electrode, to a sensor;
    at least one sensor; and,
    at least one multiplexer for selectively connecting the at least one sensor to one of the plurality of signal delivery circuits to thereby allow the sensor to sense the voltage signal indicative of a voltage at the respective electrode.

12. Apparatus according to claim 1, wherein the apparatus includes, first and second signal sources for generating respective first and second drive signals, the first and second signal sources being coupled to respective signal delivery circuits.

13. Apparatus according to claim 12, wherein the first and second signal sources are for generating at least one of:
    complementary signals;
    signals having a constant amplitude and phase; and,
    signals having a controlled amplitude and phase.

14. Apparatus according to claim 1, wherein at least one signal source is coupled to ground.

15. Apparatus according to claim 1, wherein the measurement apparatus includes at least one signal source and at least one sensor.

16. Apparatus according to claim 15, wherein the measurement apparatus is an impedance measurement apparatus.

17. A current multiplexing system comprising:
    a plurality of current multiplexers having at least one input and a plurality of outputs;
    a first and second alternating-current current source, each current source having a constant magnitude and frequency, wherein the second current source is complimentary to the first current source, and wherein each of the first and second current sources is coupled to an input of a current multiplexer;
    a plurality of current delivery circuits, each current delivery circuit having an input, a current output and a voltage output, wherein each current delivery circuit input is coupled to an output of a current multiplexer;

a plurality of electrodes, each of the plurality of electrodes being coupled to a current output of one of the plurality of current delivery circuits; and at least one voltage multiplexer having a plurality of inputs and at least one output;

wherein each current delivery circuit comprises:

a current conveyor, having an input and an output, the current conveyor input being coupled to the current delivery circuit input and the current conveyor output being coupled to the current delivery circuit current output; and a first buffer having:

a voltage buffer, having an input and an output, the voltage buffer input being coupled to the current delivery circuit current output and the voltage buffer output being coupled to the current delivery circuit voltage output;

a DC offset control circuit including an integrator coupled between the voltage buffer output and the current conveyor input; and, a negative impedance circuit coupled between the voltage buffer output and the current conveyor output, the negative impedance circuit comprising:

a compensation impedance having a compensation impedance value, a first terminal and a second terminal, the first terminal coupled to the current conveyor output; and a compensation amplifier having a compensation amplifier input, a compensation amplifier output and a gain, the compensation amplifier input coupled to the voltage buffer output, the compensation amplifier output coupled to the second terminal of the compensation impedance to provide a compensation current to flow through the impedance, and the gain and the compensation impedance values are selected based on the parasitic impedance value so that the compensation current has a magnitude substantially equal to the leakage current magnitude.

18. Apparatus for electrically connecting measurement apparatus to a biological subject, the apparatus including a signal delivery circuit including:

a first buffer having:

a first buffer input for receiving a signal from a signal source; and, a first buffer output for supplying a drive signal to an electrode attached to the biological subject;

a second buffer having:

a second buffer input coupled to the first buffer output; and, a second buffer output for providing a sensed signal indicative of a signal at the electrode, to a sensor; and, a DC offset control circuit coupled between the second buffer output and the first buffer input.

19. Apparatus according to claim 18, wherein the first buffer is a current buffer, the drive signal being a drive current.

20. Apparatus according to claim 19, wherein the current buffer is a current conveyor.

21. Apparatus according to claim 18, wherein the second buffer is a voltage buffer, the sensed signal being a voltage signal indicative of a voltage at the electrode.

22. Apparatus according to claim 18, wherein the second buffer is a current buffer, the sensed signal being indicative of a drive current.

23. Apparatus for use in performing impedance measurements on a subject, wherein the apparatus includes:

a signal source for applying a signal to a subject;

a sensor for sensing signals from the subject;

a processing system for controlling the signal source and receiving signals from the sensor; and, at least one signal delivery circuit, including:

a first buffer having:

a first buffer input for receiving a signal from a signal source; and, a first buffer output for supplying a drive signal to an electrode attached to the biological subject;

a second buffer having:

a second buffer input coupled to the first buffer output; and, a second buffer output for providing a sensed signal indicative of a signal at the electrode, to a sensor; and a DC offset control circuit coupled between the second buffer output and the first buffer input.

24. Apparatus according to claim 23, wherein the apparatus includes:

a first signal delivery circuit coupled to a drive electrode attached to the biological subject, the first signal delivery circuit including:

a first buffer having:

a first buffer input for receiving a signal from the signal source; and, a first buffer output for supplying the drive signal to the drive electrode;

a second buffer having:

a second buffer input coupled to the first buffer output; and, a second buffer output for providing a sensed signal indicative of the drive signal at the drive electrode; and a DC offset control circuit coupled between the second buffer output and the first buffer input; and a second signal delivery circuit coupled to a sense electrode attached to the biological subject, the second signal delivery circuit including:

a first buffer having:

a first buffer input coupled to ground; and, a first buffer output coupled to the sense electrode; and, a second buffer having:

a second buffer input coupled to the first buffer output;

a second buffer output for providing a sensed signal indicative of a sensed voltage at the sense electrode; and a DC offset control circuit coupled between the second buffer output and the first buffer input.

* * * * *